(12) United States Patent
Pawliszyn et al.

(10) Patent No.: US 10,545,077 B2
(45) Date of Patent: Jan. 28, 2020

(54) SOLID PHASE MICROEXTRACTION COATING

(71) Applicant: JP SCIENTIFIC LIMITED, Waterloo (CA)

(72) Inventors: Janusz Boleslaw Pawliszyn, Waterloo (CA); Emanuela Gionfriddo, Waterloo (CA); Ezel Boyaci, Kitchener (CA)

(73) Assignee: JP SCIENTIFIC LIMITED, Waterloo (CA)

(*) Notice: Subject to any disclaimer, the term of this patent is extended or adjusted under 35 U.S.C. 154(b) by 130 days.

(21) Appl. No.: 15/446,972

(22) Filed: Mar. 1, 2017

(65) Prior Publication Data

US 2017/0254732 A1     Sep. 7, 2017

Related U.S. Application Data

(60) Provisional application No. 62/302,710, filed on Mar. 2, 2016.

(51) Int. Cl.
| | |
|---|---|
| G01N 1/40 | (2006.01) |
| B01J 20/26 | (2006.01) |
| B01J 20/28 | (2006.01) |
| G01N 1/44 | (2006.01) |

(52) U.S. Cl.
CPC ............ G01N 1/405 (2013.01); B01J 20/261 (2013.01); B01J 20/28061 (2013.01); B01J 20/28064 (2013.01); G01N 1/44 (2013.01)

(58) Field of Classification Search
CPC ............... B01J 20/261; B01J 20/28061; B01J 20/28064; G01N 1/405; G01N 1/44; G01N 2001/4061

See application file for complete search history.

(56) References Cited

U.S. PATENT DOCUMENTS

| | | | |
|---|---|---|---|
| 4,140,653 A | 2/1979 | Imura et al. | |
| 4,476,231 A | 10/1984 | Deindoerfer et al. | |
| 4,616,652 A | 10/1986 | Simpson | |
| 5,047,437 A | 9/1991 | Cooke et al. | |
| 5,081,871 A | 1/1992 | Glaser | |
| 5,120,510 A | 6/1992 | Gourley et al. | |
| 5,424,187 A | 6/1995 | Shor et al. | |
| 5,460,813 A | 10/1995 | Leung et al. | |
| 5,464,395 A | 11/1995 | Faxon et al. | |
| 5,479,923 A | 1/1996 | Rantala | |
| 5,640,470 A | 6/1997 | Iyer et al. | |
| 5,691,206 A | 11/1997 | Pawliszyn | |
| 5,693,228 A | 12/1997 | Koehler et al. | |
| 5,808,300 A | 9/1998 | Caprioli | |
| 6,027,942 A | 2/2000 | Hutchens et al. | |
| 6,042,787 A | 3/2000 | Pawliszyn | |
| 6,287,521 B1 | 9/2001 | Quay et al. | |
| 6,360,588 B1 | 3/2002 | Ross et al. | |
| 6,555,813 B1 | 4/2003 | Beecher et al. | |
| 6,558,958 B1 | 5/2003 | Pilevar et al. | |
| 6,625,433 B1 | 9/2003 | Poirier et al. | |
| 6,651,124 B1 | 11/2003 | McAllister | |
| 6,689,603 B2 | 2/2004 | Pompidou et al. | |
| 6,730,096 B2 | 5/2004 | Basta et al. | |
| 6,743,180 B1 | 6/2004 | Van Bockel | |
| 6,808,937 B2 | 10/2004 | Ligler et al. | |
| 6,816,607 B2 | 11/2004 | O'Donnell et al. | |
| 6,871,556 B2 | 3/2005 | Andresen et al. | |
| 7,019,288 B2 | 3/2006 | Becker | |
| 7,110,724 B1 | 9/2006 | Epperson et al. | |
| 7,125,580 B2 | 10/2006 | Miller et al. | |
| 7,151,167 B2 | 12/2006 | Gjerde et al. | |
| 7,211,189 B2 | 5/2007 | Jinno et al. | |
| 7,232,689 B2 | 6/2007 | Pawliszyn | |
| 7,259,019 B2 | 8/2007 | Pawliszyn et al. | |
| 7,384,794 B2 | 6/2008 | Pawliszyn | |
| 7,460,589 B2 | 12/2008 | Fujimori et al. | |
| 7,468,281 B2 | 12/2008 | Kallury et al. | |
| 7,479,390 B2 | 1/2009 | Pawliszyn | |
| 7,537,803 B2 | 5/2009 | Wang et al. | |
| 7,605,003 B2 | 10/2009 | Chan et al. | |
| 7,667,010 B2 | 2/2010 | Gjerde et al. | |
| 7,738,605 B2 | 6/2010 | Mobin et al. | |
| 8,008,064 B2 | 8/2011 | Pawliszyn et al. | |

(Continued)

FOREIGN PATENT DOCUMENTS

| | | |
|---|---|---|
| CN | 2630850 Y | 8/2004 |
| CN | 102698720 A | 10/2012 |

(Continued)

OTHER PUBLICATIONS

Zhang et al. Nanocomposite teflon AF 2400 films as tunable platforms for selective transport. Anal. Chem. 2012, vol. 84, pp. 9920-9927. (Year: 2012).*

Zhao et al. How fluorous is poly(2,2-bis(trifluoromethyl)-4,5-difluoro-1,3-dioxide-co-tetrafluoroethylene) (Teflon AF)? J. Am. Chem. Soc. 2004, vol. 126, pp. 13184-13185. (Year: 2004).*

Waters Corporation. Oasis HLB product and generic method information. Water Corporation, 2003. (Year: 2003).*

Aguinaga et al., "Solid Phase Microextraction Coupled to Gas Chromatography-Mass Spectrometry for the Analysis of Famoxadone in Wines, Fruits and Vegetables," Spectroscopy Letters: An International Journal for Rapid Communication, Dec. 2009, vol. 42 (6-7), pp. 320-326.

Alpendurada., "Solid-phase Microextraction:A Promising Technique for Sample Preparation in Environmental Analysis," Journal of Chromatography. A, Aug. 2000, vol. 889(1-2), pp. 3-14.

(Continued)

*Primary Examiner* — Shafiqul Haq
(74) *Attorney, Agent, or Firm* — Borden Ladner Gervais LLP; David Nauman

(57) ABSTRACT

The present disclosure provides an extraction coating for an SPME sampling instrument, where the extraction coating includes a sorptive material immobilized in a fluorocarbon polymer that is compatible with thermal-assisted desorption techniques, solvent-assisted desorption techniques, or both. The disclosure also provides SPME sampling instruments, methods of making an SPME sampling instrument, and methods of extracting an analyte from a sample matrix using the SPME coating.

9 Claims, 4 Drawing Sheets

(56) References Cited

U.S. PATENT DOCUMENTS

| | | |
|---|---|---|
| 8,080,407 B2 | 12/2011 | Pawliszyn et al. |
| 8,114,660 B2 | 2/2012 | Pawliszyn et al. |
| 8,148,161 B2 | 4/2012 | Higgins et al. |
| 8,206,902 B2 | 6/2012 | Mitani et al. |
| 8,362,219 B2 | 1/2013 | Gjerde et al. |
| 8,364,033 B2 | 1/2013 | Skoog et al. |
| 8,399,055 B2 | 3/2013 | Bakry et al. |
| 8,494,236 B2 | 7/2013 | Jolly et al. |
| 8,538,098 B2 | 9/2013 | Jacob et al. |
| 8,598,325 B2 | 12/2013 | Pawliszyn |
| 8,620,233 B2 | 12/2013 | Brobston |
| 9,108,217 B2 | 8/2015 | Hoerr et al. |
| 9,502,226 B2 | 11/2016 | Brown et al. |
| 2002/0034827 A1 | 3/2002 | Singh et al. |
| 2002/0142745 A1 | 10/2002 | Kang et al. |
| 2003/0135195 A1 | 7/2003 | Jimenez et al. |
| 2003/0180954 A1 | 9/2003 | Riviere et al. |
| 2003/0183758 A1 | 10/2003 | Colburn et al. |
| 2004/0005582 A1 | 1/2004 | Shipwash |
| 2004/0191537 A1 | 9/2004 | Lubda et al. |
| 2004/0224362 A1 | 11/2004 | Gjerde et al. |
| 2004/0241721 A1 | 12/2004 | Gjerde et al. |
| 2005/0032237 A1 | 2/2005 | Sandra et al. |
| 2005/0112650 A1 | 5/2005 | Chang et al. |
| 2005/0133714 A1 | 6/2005 | Vestal et al. |
| 2005/0142033 A1 | 6/2005 | Glezer et al. |
| 2007/0243843 A1 | 10/2007 | Shalash |
| 2008/0023630 A1 | 1/2008 | Boschetti et al. |
| 2008/0193772 A1 | 8/2008 | Agroskin et al. |
| 2008/0242249 A1 | 10/2008 | Gomez et al. |
| 2009/0026122 A1 | 1/2009 | Pawliszyn et al. |
| 2009/0058531 A1 | 3/2009 | Hwang et al. |
| 2009/0190811 A1 | 7/2009 | Zheng et al. |
| 2009/0232369 A1 | 9/2009 | Senegas et al. |
| 2009/0317916 A1 | 12/2009 | Ewing et al. |
| 2010/0130796 A1 | 5/2010 | Combes et al. |
| 2010/0144049 A1 | 6/2010 | Combes et al. |
| 2010/0249591 A1 | 9/2010 | Heimdal et al. |
| 2010/0322496 A1 | 12/2010 | Liu et al. |
| 2012/0004005 A1 | 1/2012 | Ahmed et al. |
| 2012/0078097 A1 | 3/2012 | Wang et al. |
| 2012/0199735 A1 | 8/2012 | Krechmer et al. |
| 2012/0228228 A1 | 9/2012 | Pawliszyn et al. |
| 2013/0051647 A1 | 2/2013 | Miao et al. |
| 2013/0182935 A1 | 7/2013 | Wang et al. |
| 2014/0017693 A1 | 1/2014 | Mao et al. |
| 2014/0040220 A1 | 2/2014 | Kimura et al. |
| 2014/0164715 A1 | 6/2014 | Weiner et al. |
| 2014/0346348 A1 | 11/2014 | Krechmer et al. |
| 2015/0011376 A1 | 1/2015 | Pawliszyn et al. |
| 2015/0068280 A1 | 3/2015 | Ricoul |
| 2015/0231602 A1 | 8/2015 | Pawliszyn |
| 2015/0318158 A1 | 11/2015 | Pawliszyn et al. |
| 2015/0318160 A1 | 11/2015 | Pawliszyn et al. |
| 2015/0364310 A1 | 12/2015 | Musselman |
| 2015/0369712 A1 | 12/2015 | Pawliszyn et al. |

FOREIGN PATENT DOCUMENTS

| | | |
|---|---|---|
| CN | 102847524 A | 1/2013 |
| DE | 19905239 A1 | 8/2000 |
| EP | 1618592 A2 | 1/2006 |
| JP | H1164277 A | 3/1999 |
| JP | 2009539114 A | 11/2009 |
| WO | 9115745 A1 | 10/1991 |
| WO | 0068665 A1 | 11/2000 |
| WO | 03075772 A3 | 9/2003 |
| WO | 2010008450 A2 | 1/2010 |

OTHER PUBLICATIONS

Anastassiades et al., "Fast and Easy Multiresidue Method Employing Acetonitrile Extraction/partitioning and "Dispersive Solid-phase Extraction" for the Determination of Pesticide Residues in Produce," Journal of AOAC International, Mar. 2003, vol. 86 (2), pp. 412-431.

Augusto et al., "New Sorbents for Extraction and Microextraction Techniques," Journal of Chromatography A, Apr. 2010, vol. 1217 (16), pp. 2533-2542.

Banerjee et al., "Validation and Uncertainty Analysis of a Multi-Residue Method for Pesticides in Grapes Using Ethyl Acetate Extraction and Liquid Chromatography—Tandem Mass Spectrometry," Journal of Chromatography A, Nov. 2007, vol. 1173 (1-2), pp. 98-109.

Beltran et al., "Solid-Phase Microextraction in Pesticide Residue Analysis," Journal of Chromatography A, Jul. 2000, vol. 885 (1-2), pp. 389-404.

Bistoquet et al., "Left Ventricular Deformation Recovery From Cine MRI Using an Incompressible Model," IEEE Transactions on Medical Imaging, Sep. 2007, vol. 26 (9), pp. 1136-1153.

Boos et al., "Alkyl-diol Silica (ADS): Restricted Access Precolumn Packing for Direct Injection and Coupled-column Chromatography of Biofluids," Fresenius' Journal of Analytical Chemistry, Jan. 1995, vol. 352 (7), pp. 684-690.

Cai et al., "Vinyl Crown Ether as a Novel Radical Crosslinked Sol-Gel SPME Fiber for Determination of Organophosphorus Pesticides in Food Samples," Analytica Chimica Acta, Feb. 2006, vol. 559 (1), pp. 89-96.

Capobiango et al., "A Solid Phase Microextraction Method for the Chromatographic Determination O Organophosphorous Pesticides in Fish, Water, Potatoes, Guava and Coffee," Journal of Brazilian Chemical Society, Oct. 2005, vol. 16 (5), pp. 907-914.

Charlton et al., "Determination of Imisazole and Triazole Fungicide Residues in Honeybees Using Gas Chromatography-Mass Spectrometry," Journal of Chromatography A, Feb. 2007, vol. 1141 (1), pp. 117-122.

Chen, et al., "High Extraction Efficiency for Polar Aromatic Compounds in Natural Water Samples using Multiwalled Carbon Nanotubes/Nafion Solid-Phase Microextraction Coating," Journal of Chromatography A, Jul. 2009, vol. 1216 (52), pp. 9143-9148.

Chen et al., "Solid Phase Microextraction Coupled to High-Performance Liquid Chromatography," Analytical Chemistry, Aug. 1995, vol. 67 (15), pp. 2530-2533.

Chen et al., "The Application of Solid Phase Microextraction in the Analysis of Organophosphorous Pesticides in a Food Plant," Environmental Science and Technology, Dec. 1998, vol. 32 (23), pp. 3816-3820.

Chipuk et al., "The Influence of Material and Mesh Characteristics on Transmission Mode Desorption Electrospray Ionization," Journal of the American Society for Mass Spectrometry, Apr. 2009, vol. 20 (4), pp. 584-592.

Chipuk et al., "Transmission Mode Desorption Electrospray Ionization," Journal of the American Society for Mass Spectrometry, Nov. 2008, vol. 19 (11), pp. 1612-1620.

Cunha et al., "Fast Low-Pressure Gas Chromatography-mass Spectrometry Method for the Determination of Multiple Pesticides in Grapes, Musts and Wines," Journal of Chromatography A, Jan. 2009, vol. 1216 (1), pp. 119-126.

De Jager et al., "Analysis of Tetramethylene Disulfotetramine in Foods Using Solid-Phase Microextraction-Gas Chromatography-Mass Spectrometry," Journal of Chromatography A, May 2008, vol. 1192 (1), pp. 36-40.

Deng et al., "Strategies for Coupling Solid-Phase Microextraction with Mass Spectometry," Trends in Analytical Chemistry, Mar. 2014, vol. 55, pp. 55-67.

Dietz et al., "Recent Developments in Solid Phase Microextraction Coatings and Related Techniques," Journal of Chromatography A, Jan. 2006, vol. 1103 (2), pp. 183-192.

Djozan et al., "Preparation and Biding Study of Solid Phase Microextraction Fiber on the Basis of Ametryn-Imprinted Polymer—Application to the Selective Extraction of Persistent Triazine Herbicides in Tap Water, Rice, Maize and Onion," Journal of Chromatography A, Mar. 2009, vol. 1216 (12), pp. 2211-2219.

(56) References Cited

OTHER PUBLICATIONS

Frangi et al., "Three-Dimensional Modeling for Functional Analysis of Cardiac Images: A Review," IEEE Transactions on Medical Imaging, Jan. 2001, vol. 20 (1), 24 pages.
Frerot et al., "Solid-Phase Microextraction (SPME): A New Tool in Pheromone Identification in Lepidoptera," Journal of High Resolution Chromatography, Jun. 1997, vol. 20 (6), pp. 340-342.
Furlong et al., "Routine Determination of Sulfonylurea, Imidazolinone, and Sulfonamide Herbicides at Nanogram-Per-Liter Concentrations by Solid-Phase Extraction and Liquid Chromatography/Mass Spectrometry," The Science of the Total Environment, Apr. 2000, vol. 248 (2-3), pp. 135-146.
Fytianos et al., "Solid Phase Microextraction Applied to the Analysis of Organophosphorus Insecticides in Fruits," Chemosphere, Dec. 2006, vol. 65 (11), pp. 2090-2095.
Gomez-Rios et al., "Solid Phase Microextraction (SPME)-Transmission Mode (TM) Pushes Down Detection Limits in Direct Analysis in Real Time (DART)," Chemical Communications, Aug. 2014, vol. 50, pp. 12937-12940.
Gonzalez-Rodriguez et al., "Multiresidue Determination of 11 New Fungicides in Grapes and Wines by Liquid-Liquid Extraction/Clean-Up and Programmable Temperature Vaporization Injection with Analyte Protectants/Gas Chromatography/Ion Trap Mass Spectrometry," Journal of Chromatography A, Aug. 2009, vol. 1216 (32), pp. 6033-6042.
Guillet et al., "Microwave/SPME Method to Quantify Pesticides Residues in Tomato Fruits," Journal of Environmental Science and Health, Part B: Pesticides, Food Contaminents, Jun. 2009, vol. 44 (5), pp. 415-422.
Heinze, "Ultramicroelectrodes in Electrochemistry," Angewandte Chemie International Edition in English, Sep. 1993, vol. 32 (9), pp. 1268-1288.
Hu et al., "Solid Phase Microextraction of Pesticide Residues from Strawberries," Food Additives and Contaminants, Mar. 1999, vol. 16 (3), pp. 111-117.
Hu et al., "Solid-phase Microextraction of Phenol Compounds Using a Fused-Silica Fiber Coated with beta-Cyclodextrin-bonded Silica Particles", Analytical Sciences, Apr. 2004, vol. 20, pp. 667-671.
International Patent Application No. PCT/CA2017/050279, International Search Report and Written Opinion dated May 12, 2017.
Jackson et al., "Mass Spectrometry for Genotyping: An Emerging Tool for Molecular Medicine," Molecular Medicine Today, Jul. 2000, vol. 6 (7), pp. 271-276.
Jahnke et al., "Do Complex Matrices Modify the Sorptive Properties of Polydimethylsiloxane (PDMS) for Non-Polar Organic Chemicals," Journal of Chromatography A, Jul. 2010, vol. 1217 (29), pp. 4765-4770.
Kataoka et al., "Applications of Solid-Phase Microextraction in Food Analysis," Journal of Chromatography A, Jun. 2000, vol. 880 (1-2), pp. 35-62.
Kloskowski, et al, "Membrane Solid-phase Microextraction—A New Concept of Sorbent Preparation," Analytical Chemistry, Sep. 2009, vol. 81 (17), pp. 7363-7367.
Lambropoulou et al., "Headspace Solid-Phase Microextraction in Combination with Gas Chromatography-Mass Spectrometry for the Rapid Screening of Organophosphorus Insecticide Residues in Strawberries and Cherries," Journal of Chromatography A, Apr. 2003, vol. 993 (1-2), pp. 197-203.
Lambropoulou et al., "Validation of an SPME Method, Using PDMS, PA, PDMS-DVB, and CW-DVB SPME Fiber Coatings, for Analysis of Organophosphorus Insecticides in Natural Waters," Analytical and Bioanalytical Chemistry, Nov. 2002, vol. 374 (5), pp. 932-941.
Lavaud et al., "Optimal Anticoagulation Strategy in Haemodialysis With Heparin-coated Polyacrylonitrile Membrane," Nephrology Dialysis Transplantation, Oct. 2003, vol. 18 (10), pp. 2097-2104.
Lord et al., "Development and Evaluation of a Solid-Phase Microextraction Probe for in Vivo Pharmacokinetic Studies," Analytical Chemistry, Oct. 2003, vol. 75 (19), pp. 5103-5115.
Louch et al., "Dynamics of Organic Compound Extraction from Water Using Liquid-Coated Fused Silica Fibers," Analytical Chemistry, May 1992, vol. 64 (10), pp. 1187-1199.
Martos et al., "Calibration of Solid Phase Microextraction for Air Analyses Based on Physical Chemical Properties of the Coating," Analytical Chemistry, Jan. 1997, vol. 69 (2), pp. 206-215.
Menezes et al., "Development, Validation and Application of a Methodology Based on Solid-Phase Micro Extraction Followed by Gas Chromatography Coupled to Mass Spectrometry (SPME/GC-MS) for the Determination of Pesticide Residues in Mangoes," Talanta, Apr. 2010, vol. 81 (1-2), pp. 346-354.
Mindrup et al., "Improved Performance of SPME Fibers and Applications," SUPELCO, Sigma-Aldrich Co., 2001, pp. 1-25.
Mirnaghi et al., "Optimization of the Coating Procedure for a High-Throughput 96-Blade Solid Phase Microextraction System Coupled with LC-MS/MS for Analysis of Complex Samples," Analytical Chemistry, Jun. 2011, vol. 83 (15), pp. 6018-6025.
Mirnaghi et al., "Reusable Solid-Phase Microextraction Coating for Direct Immersion whole-Blood Analysis and Extracted Blood Spot Sampling Coupled with Liquid Chromatography-Tandem Mass Spectrometry and Direct Analysis in Real Time-Tandem Mass Spectrometry", Analytical Chemistry, Aug. 2012, vol. 84 (19), pp. 8301-8309.
Moder et al., "Determination of urinary acylcarnitines by ESI-MS coupled with solid-phase microextraction (SPME)", Journal of Mass Spectrometry, Jul. 1997, vol. 32, pp. 1195-1204.
Moneti et al., "Solid-Phase Microextraction of Insect Epicuticular Hydrocarbons for Gas Chromatographic/Mass Spectrometric Analysis," Rapid Communications in Mass Spectrometry, May 1997, vol. 11 (8), pp. 857-862.
Mullett et al., "Direct Determination of Benzodiazepines in Biological Fluids by Restricted-Access Solid-Phase Microextraction," Analytical Chemistry, Mar. 2002, vol. 74 (5), pp. 1081-1087.
Musteata, "Biocompatible Solid Phase Microextraction," Thesis, Master in Science, University of Waterloo, Waterloo, Ontario, Canada, 2006, pp. i-xi and 1-70.
Musteata et al., "Biocompatible Solid-Phase Microextraction Coatings Based on Polyacrylonitrile and Solid-Phase Extraction Phases," Analytical Chemistry, Sep. 2007, vol. 79 (18), pp. 6903-6911.
Namera et al., "Analysis of Anatoxin-A in Aqueous Samples by Solid-phase Microextraction Coupled to High-performance Liquid Chromatography with Fluorescence Detection and On-Fiber Derivatization," Journal of Chromatography A, Jul. 2002, vol. 963 (1-2), pp. 295-302.
Natangelo et al., "Evaluation of Solid Phase Microextraction-Gas Chromatography in the Analysis of Some Pesticides With Different Mass Spectrometric Techniques: Application to Environmental Waters and Food Samples," Analytical Letters, Feb. 2002, vol. 35 (2), pp. 327-338.
Nie et al., "Preparation and Characterization of Polyacrylonitrile-Based Membranes: Effects of Internal Coagulant on Poly (Acrylonitrile-co-maleic Acid) Ultrafiltration Hollow Fiber Membranes," Desalination, Jan. 2004, vol. 160 (1), pp. 43-50.
Oliva et al., "Determination of Chlorpyrifos, Penconazole, Fenarimol, Vinclozolin and Metalaxyl in Grapes, Must and Wine by On-Line Microextraction and Gas Chromatogaphy," Journal of Chromatography A, Feb. 1999, vol. 833 (1), pp. 43-51.
Oliva et al., "Multiresidue Method for the Rapid Determination of Organophosphorus Insecticides in Grapes, Must and Wine," Journal of Chromatography A, Jun. 2000, vol. 882 (1-2), pp. 213-220.
Pawliszyn J., "SPME Method Development" in: Solid Phase Microextraction: Theory and Practice, 1st Edition. New York: Wiley-VCH, 1997, pp. 97-139.
Paya et al., "Analysis of Pesticide Residues Using the Quick Easy Cheap Effective Rugged and Safe (QuEChERS) Pesticide Multiresidue Method in Combination With Gas and Liquid Chromatography and Tandem Mass Spectrometric Detection," Analytical and Bioanalytical Chemistry, Nov. 2007, vol. 389 (6), pp. 1697-1714.
Perez et al., "Transmission-Mode Direct Analysis in Real Time and Desorption Electrospray Ionization Mass Spectrometry of Insecticide-Treated Bednets for Malaria Control," Analyst, Feb. 2010, vol. 135, pp. 712-719.

(56) References Cited

OTHER PUBLICATIONS

Poerschmann et al., "Solid Phase Microextraction for Determining the Distribution of Chemicals in Aqueous Matrices," Journal of Analytical Chemistry, Feb. 1997, vol. 69 (4), pp. 597-600.
Reubsaet et al., "Determination of Benzodiazepines in Human Urine and Plasma with Solvent Modified Solid Phase Micro Extraction and Gas Chromatography; Rationalisation of Method Development Using Experimental Design Strategies," Journal of Pharmaceutical and Biomedical Analysis, Dec. 1998, vol. 18 (4-5), pp. 667-680.
Ridgway et al., "Sample Preparation Techniques for the Determination of Trace Residues and Contaminants in Food," Journal of Chromatography A, Jun. 2007, vol. 1153 (1-2), pp. 36-53.
Risticevic et al., "Protocol for Solid-Phase Microextraction Method Development," Nature Protocols, Jan. 2010, vol. 5 (1), pp. 122-139.
Rodriguez-Lafuente et al., "Determination of Cocaine and Methadone in Urine Samples by Thin-Film Solid-Phase Microextraction and Direct Analysis in Real Time (DART) Coupled With Tandem Mass Spectrometry," Analytical and Bioanalytical Chemistry, Dec. 2013, vol. 405 (30), pp. 9723-9727.
Schurek et al., "Application of Head-Space Solid-Phase Microextraction Coupled to Comprehensive Two-dimensional Gas Chromatography-Time-of-Flight Mass Spectrometry for the Determination of Multiple Pesticide Residues in Tea Samples," Analytica Chimica Acta, Mar. 2008, vol. 611 (2), pp. 163-172.
Shirey, "Optimization of Extraction Conditions and Fiber Selection for Semivolatile Analytes Using Solid-Phase Microextraction," Journal of Chromatographic Science, Jul. 2000, vol. 38 (7), pp. 279-288.
Sigma-Aldrich, SPME Sample Prep Made Easy, How to Choose the Proper SPME Fiber, Newsletter, Sigma-Aldrich, Supelco, Supelco Park, Bellefonte, PA 16823-0048, Fall 1999, 4 pages.
Simplicio et al., "Validation of a Solid-Phase Microextraction Method for the Determination of Organophosphorus Pesticides in Fruits and Fruit Juice," Journal of Chromatography A, Feb. 1999, vol. 833 (1), pp. 35-42.
Smith et al., "Solid-Phase Microextraction as a Tool for Studying Volatile Compounds in Frog Skin," Chemistry and Ecology, Dec. 2000, vol. 17 (3), pp. 215-225.
Spottiswoode et al., "Motion-guided segmentation for cine DENSE MRI," Medical Image Analysis, Feb. 2009, vol. 13 (1), pp. 105-115.
Steiniger et al., "Determination of Multiresidue Pesticides in Green Tea by Using a Modified QuEChERS Extraction and Ion-Trap Gas Chromatography/Mass Spectrometry," Journal of AOAC International, Jul. 2010, vol. 93 (4), pp. 1169-1179.
Turiel et al., "Molecularly Imprinted Polymeric Fibers for Solid Phase Microextraction," Analytical Chemistry, Apr. 2007, vol. 79 (8), pp. 3099-3104.
Vail et al., "Rapid and Unambiguous Identification of Melamine in Contaminated Pet Food Based on Mass Spectrometry with Four Degrees of Confirmation", Journal of Analytical Toxicology, Jul. 2007, vol. 31 (6), pp. 304-312.
Vinas et al., "Method Development and Validation for Strobilurin Fungicides in Baby Foods by Solid-Phase Microextraction Gas Chromatography-Mass Spectrometry," Journal of Chromatography A, Jan. 2009, vol. 1216 (1), pp. 140-146.
Volante et al., "Application of Solid Phase Micro-Extraction (SPME) to the Analysis of Pesticide Residues in Vegetables," Pest Management Science, Jul. 2000, vol. 56 (7), pp. 618-636.
Vuckovic et al., "In Vitro Evaluation of New Biocompatible Coatings for Solid-Phase Microextraction: Implications for Drug Analysis and in Vivo Sampling Applications," Analytica Chimica Acta, Apr. 2009, vol. 638 (2), pp. 175-185.
Wahba, "Spine Interpolation and Smoothing on the Sphere," SIAM Journal on Scientific and Statistical Computing (Society for Industrial and Applied Mathematics), Mar. 1981, vol. 2 (1), pp. 5-16.
Wang et al., "Surface Confined Ionic Liquid as a Stationary Phase for HPLC," The Analyst, Jul. 2006, vol. 131 (9), pp. 1000-1005.
Whang et al., "Solid Phase Microextraction Coupled to Capillary Electrophoresis," Analytical Communications, 1998, vol. 35, pp. 353-356.
Wong et al., "Development and Interlaboratory Validation of a QuEChERS-Based Liquid Chromatography-Tandem Mass Spectrometry Method for Multiresidue Pesticide Analysis," Journal of Agricultural and Food Chemistry, Mar. 2010, vol. 58 (10), pp. 5897-5903.
Yang et al., "Surface Modification and Blood Compatibility of Polyacrylonitrile Membrane with Immobilized Chitosan-Heparin Conjugate," Journal of Polymer Research, Sep. 2002, vol. 9 (3), pp. 201-206.
Zambonin et al., "Solid Phase Microextraction and Gas Chromatography-mass Spectrometry for the Rapid Screening of Triazole Residues in Wine and Strawberries," Journal of Chromatography A, Aug. 2002, vol. 967 (2), pp. 255-260.
Zambonin et al., "Solid Phase Microextraction-Gas Chromatography Mass Spectrometry: A Fast and Simple Screening Method for the Assessment of Organophosphorus Pesticides Residues in Wine and Fruit Juices," Food Chemistry, Jun. 2004, vol. 86 (2), pp. 269-274.
Zeng et al., "An Electrochemically Enhanced Solid-Phase Microextraction Approach Based on a Multi-Walled Carbon Nanotubes/Nafion Composite Coating," Journal of Chromatography A, Jan. 2010, vol. 1217(11), pp. 1735-1741.
Zeng et al., "Determination of Amphetamines in Biological Samples using Electro Enhanced Solid-Phase Microextraction-Gas Chromatography," Journal of Chromatography B, Jul. 2015, vol. 1000, pp. 169-175.
Zeng et al., "Development of Polymethylphenylsiloxane-Coated Fiber for Solid-Phase Microextraction and its Analytical Application of Qualitative and Semi-Quantitative of Organochlorine and Pyrethroid Pesticides in Vegetables," Analytica Chimica Acta, Jun. 2008, vol. 619 (1), pp. 59-66.
Zeng et al., "Ordered Mesoporous Carbon/Nafion as a Versatile and Selective Solid-Phase Microextraction Coating," Journal of Chromatography A, Sep. 2014, vol. 1365, pp. 29-34.
Zhang et al., "Solid-Phase Microextraction," Analytical Chemistry, Sep. 1994, vol. 66 (17), pp. 844A-853A.
Abolghasemi Mir Mahdi et al., "Efficient solid-phase microextraction of triazole pesticides from natural water samples using a Nafion-loaded trimethylsilane-modified mesoporous silica coating of type SBA-15", Mikrochimica Acta, Springer Verlag, Vienna, AT, vol. 183, No. 2, Dec. 30, 2015, pp. 889-895.
Hong Zhang et al., "Nanocomposite Teflon AF 2400 Films as Tunable Platforms for Selective Transport", Analytical Chemistry, vol. 84, No. 22, Nov. 8, 2012, pp. 9920-9927.
Vincent Bessonneau et al., "In vivo solid phase microextraction sampling of human saliva for non-invasive and on-site monitoring", Analytica Chimica Acta, vol. 856, Dec. 3, 2014, pp. 35-45.
European Application No. 17759046.0, European Search Report dated Sep. 20, 2019.

* cited by examiner

SOLID PHASE MICROEXTRACTION COATING

CROSS-REFERENCE TO RELATED APPLICATIONS

This application claims the benefit of priority of U.S. Provisional Patent Application No. 62/302,710 filed Mar. 2, 2016, which is hereby incorporated by reference.

FIELD

The present disclosure relates to solid phase microextraction coatings.

BACKGROUND

The following paragraphs are not an admission that anything discussed in them is prior art or part of the knowledge of persons skilled in the art.

Solid phase microextraction (SPME) is an approach for sample preparation that may be used in various analytical methods. SPME devices include an extraction coating present on a support. The extraction coating includes adsorptive or absorptive particles, which may have different geometries. Exposure of the SPME device directly into a matrix or into its headspace, for a certain period of time, extracts and enriches analytes contained in the sample matrix.

The SPME process is governed by the partitioning of analytes from the matrix onto or into the extraction phase, and extraction efficiency of an analyte depends on the analyte's affinity toward the adsorptive or absorptive particles present in the extraction coating.

After extraction and enrichment of the analytes onto or into the extraction phase, the SPME device may be placed in an analytical device where the analytes are desorbed and analyzed. Alternatively, the analytes may be desorbed separately and analyzed separately.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims, SPME integrates sampling and sample preparation into a single step. Because of this, the SPME coating must be compatible with the sample matrix, the analytical device, and the desorption process used by or before the analytical device. It is also desirable for the SPME device to be capable of being used multiple times without degrading, without accumulating components of the matrix that could generate errors or incorrect readings in the analytical device, or both.

It is desirable to develop an SPME coating that addresses or ameliorates one or more shortcomings associated with known SPME coatings. For example, it is desirable to develop an SPME coating that is: (a) compatible with a plurality of different sample matrixes, (b) compatible with a sample matrix that was previously incompatible with SPME devices, (c) compatible with a plurality of different analytical devices, (d) compatible with an analytical device that was previously incompatible with SPME devices, (e) compatible with a plurality of different desorption methods, (f) compatible with a desorption method that was previously incompatible with SPME devices, or (g) any combination thereof.

Desorption of the analytes may be followed by a detection step (such as mass spectrometry), with an optional separation step (such as chromatography) in between. In some examples, the analyte may be directly desorbed from the SPME coating and transferred to the detector (such as a mass spectrometer) while omitting a separation step. Analytes that are adsorbed or absorbed onto or into the SPME coating may be desorbed using thermal-assisted desorption, solvent-assisted desorption, or both. The method of desorption may be determined by the separation/detection system, by the SPME coating, or both. For example, an SPME coating may not be compatible with thermal desorption if the coating is thermally labile; and/or may not be compatible with organic solvent-assisted desorption if the chemical composition of the coating changes on exposure to the organic solvent. An SPME coating that may be used in both thermal desorption and solvent desorption may be used, for example, in both liquid- and gas-chromatographic applications, thus broadening the amount of chemical information that can be obtained from a sample matrix.

An SPME coating according to the present disclosure may be compatible with a biological sample that includes macromolecules and/or other biological components. Such an SPME coating may reduce or eliminate accumulation of the macromolecules and/or matrix components on their surface. SPME coatings with such matrix compatibility features may provide greater extraction and/or more accurate analysis of medium- to low-volatile analytes, such as analytes from in-tissue or in vivo samples. For example, such an SPME coating may be useful in metabolomics or untargeted analysis, where it is desirable for the coating to extract a broad range of medium- to low-volatile analytes, while also reducing or eliminating accumulation of the macromolecules and/or matrix components on the coating surface, and being compatible with different desorption strategies in order to identify the different analytes.

The present disclosure provides an SMPE coating that attempts to address or ameliorate one or more shortcomings involved with known SPME coatings. SPME coatings according to the present disclosure include an extraction coating that has particulate sorptive material immobilized in a fluorocarbon polymer that is compatible with thermal-assisted desorption techniques, solvent-assisted desorption techniques, or both.

Fluorocarbon polymers are typically characterized as non-interactive with non-fluorocarbon material. However, the authors of the present disclosure surprisingly determined that fluorocarbon polymers according to the present disclosure were able to anchor non-fluorocarbon based particulate sorptive material to a support. Further, fluorocarbon polymers are hydrophobic. Accordingly, the fluorocarbon polymers were not expected to properly embed particulate sorptive material having polar character and anchor them to the support. Even more surprisingly, the authors determined that polar particulate sorptive material could be embedded.

In another aspect, the present disclosure provides a SPME sampling instrument that includes a support, and an extraction coating covering at least a portion of the support. The extraction coating includes particulate sorptive material immobilized in a fluorocarbon polymer that is compatible with thermal-assisted desorption techniques, solvent-assisted desorption techniques, or both.

In yet another aspect, the present disclosure provides a method of making an SPME coating. The method includes mixing a fluorocarbon polymer and a particulate sorptive material in a solvent; applying the mixture to a support to form a substantially uniform SPME coating layer; and removing the solvent. The solvent may be a fluorocarbon-based fluid. The fluorocarbon polymer may be soluble in the fluorocarbon-based fluid, which allows the coating layer to be formed without curing the fluorocarbon polymer.

In still another aspect, the present disclosure provides a method of extracting an analyte from a sample, such as a small molecule analyte. The method includes exposing an SPME sampling instrument to the analyte, where the SPME sampling instrument includes a support, and an extraction coating covering at least a portion of the support. The extraction coating includes particulate sorptive material immobilized in a fluorocarbon polymer that is compatible with thermal-assisted desorption techniques, solvent-assisted desorption techniques, or both. The authors of the present disclosure determined that exemplary sampling instruments were capable of extracting analytes (with a broad range of polarity and/or molecular weight) from biological matrixes, which contain macromolecules such as proteins and cells, without acting as a barrier for the analytes.

The authors of the present disclosure determined that the combination of exemplary hydrophilic-lipophilic-balance (HLB) particles and at least one exemplary fluorocarbon polymer could be used in gas chromatography, liquid chromatography, capillary electrophoresis, and direct coupling to an analytical instrument (such as a mass spectrometer) by omitting chromatographic separation.

In one aspect, the present disclosure provides a solid-phase micro-extraction (SPME) coating that includes a sorptive particulate material immobilized in a fluorocarbon polymer that is compatible with a thermal-assisted desorption technique, a solvent-assisted desorption technique, or both.

The fluorocarbon polymer may comprises a polymer formed from the polymerization of a fluorocarbon monomer or a mixture of monomers that include a fluorocarbon monomer. The fluorocarbon monomer may be: vinyl fluoride (VF1), vinylidene fluoride (VDF), tetrafluoroethylene (TFE), hexafluoropropylene (HFP), perfluoropropylvinylether (PPVE), perfluoromethylvinylether (PMVE), or chlorotrifluoroethylene (CTFE); or the mixture of monomers comprises: vinyl fluoride (VF1), vinylidene fluoride (VDF), tetrafluoroethylene (TFE), hexafluoropropylene (HFP), perfluoropropylvinylether (PPVE), perfluoromethylvinylether (PMVE), chlorotrifluoroethylene (CTFE), or a combination thereof, and optionally ethylene (E) and/or propylene (P).

The fluorocarbon polymer may be a polymer of, or a copolymer that includes: a polytetrafluoroethylene (PTFE), a fluorinated ethylene-propylene (FPE), a fluoroelastomer [tetrafluoroethylene-propylene] (FEPM), or any combination thereof.

The fluorocarbon polymer may be a copolymer of tetrafluoroethylene and 2,2-bistrifluoromethyl-4,5-difluoro-1,3-dioxole, such as a copolymer in the ratio of 13:87 or a copolymer in the ratio of 35:65.

The fluorocarbon polymer may have: a thermal stability up to 320° C.; a chemical stability towards a non-fluorinated solvent such as: a short chain alcohol, a hydrocarbon (for example an aliphatic, a cyclic, or an aromatic hydrocarbon), water, a chlorinated solvent, an ester, an ether, a nitrile, or any combination thereof; a chemical stability towards a solvent having a pH from 0.01 to 14; or any combination thereof.

The fluorocarbon polymer may be a mixture of polymers,

The fluorocarbon polymer may have carbon-fluorine (C—F) bonds and carbon-hydrogen (C—H) bonds, wherein fewer than 5% of all the C—F and C—H bonds in the fluorocarbon polymer are C—H bonds. In some examples, the fluorocarbon polymer may have substantially no C—H bonds.

The sorptive material may be a porous material having mesa-, macro-, or micro-pores. At least 80% of the pores may have a diameter from about 10 Å to about 10,000 Å.

The sorptive material may be a porous material having pores with diameters from about 100 Å to about 180 Å. At least 80% of the pores may have a diameter from about 100 Å to about 180 Å.

The sorptive material may have a surface area of about 10 $m^2/g$ to about 3000 $m^2/g$, such as about 200 $m^2/g$ to about 800 $m^2/g$.

The sorptive material may include particles, nanosheets, nanotubes, or any combination thereof. The sorptive material may be inorganic, organic, a hybrid inorganic/organic material, or a mixture of both inorganic and organic materials.

The particles may have diameters from about 1 nm to about 100 μm, such as from about 3 μm to about 10 μm, or from about 3 μm to about 7 μm. The nanosheets may have thicknesses from about 1 nm to about 100 nm. The nanotubes may have diameters from about 1 nm to about 10 nm, such as from about 4 nm to about 6 nm.

The sorptive material may include: normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balance (HLB) particles, carboxen 1006 particles, carbowax particles, divinylbenzene (DVB) particles, octadecylsilane particles, nanoparticles, processed mineral based particles, carbon nanotubes, functionalized-carbon nanotubes, graphene, graphene oxide, functionalized-graphene, quantum dots, organic polymeric particles optionally functionalized with an organic moiety (such as a carbon chain, a strong cation moiety, a weak cation moiety, a strong anion moiety, or a weak anion moiety), inorganic polymeric particles optionally functionalized with an organic moiety (such as a carbon chain, a strong cation moiety, a weak cation moiety, a strong anion moiety, or a weak anion moiety), or any combination thereof.

In some examples, the sorptive material may include hydrophilic-lipophilic-balance particles, such as particles comprising the copolymerization polymer product of N-vinylpyrrolidinone and divinylbenzene.

The fluorocarbon polymer may be a copolymer of tetrafluoroethylene and 2,2-bistrifluoromethyl-4,5-difluoro-1,3-dioxole in the ratio of 13:87; and the sorptive material may include hydrophilic-lipophilic-balance particles comprising the copolymerization polymer product of N-vinylpyrrolidinone and divinylbenzene.

The coating may have an average thickness from about 5 μm to about 500 μm.

The coating may have a homogeneous coating surface.

In another aspect, the present disclosure provides a solid-phase micro-extraction (SPME) sample instrument that includes: a support; and an extraction coating as discussed above covering at least a portion of the support.

The support may be a metal support, a metal alloy support, a fused silica support, a plastic support, a fluoroplastic support, or a carbon material support. The carbon material support may be a carbon fiber fabric. The support may include stainless steel, titanium, or a nickel-titanium alloy such as nitinol.

The support may be shaped in the form of a needle, a mesh fabric, a metallic mesh, or a blade.

In another aspect, the present disclosure provides a method of making a solid-phase micro-extraction (SPME) sample instrument. The method includes: mixing a fluorocarbon polymer and a sorptive material in a solvent; applying the mixture to a support to form a substantially uniform SPME coating layer on at least a portion of the support; and removing the solvent.

The solvent may include a fluorocarbon-based fluid. The fluorocarbon-based fluid may include perfluorohexane, perfluoro(2-butyl-tetrahydrofurane), perfluorotripentylamine, or a combination thereof.

The solvent may include a perfluoro-polyether.

The solvent may include a non-fluorocarbon-based fluid. The fluorocarbon-based fluid and the non-fluorocarbon-based fluid may be in sufficient amounts to form an emulsion capable of acting as a porogen for the fluorocarbon polymer coating layer.

The method may include successively applying a plurality of layers of the mixture to form the SPME coating layer.

The sorptive material may include normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balance (HLB) particles, carboxen 1006 particles, carbowax particles, divinylbenzene (DVB) particles, octadecylsilane particles, nanoparticles, processed mineral based particles, carbon nanotubes, functionalized-carbon nanotubes, graphene, graphene oxide, functionalized-graphene, quantum dots, organic polymeric particles optionally functionalized with an organic moiety (such as a carbon chain, a strong cation moiety, a weak cation moiety, a strong anion moiety, or a weak anion moiety), inorganic polymeric particles optionally functionalized with an organic moiety (such as a carbon chain, a strong cation moiety, a weak cation moiety, a strong anion moiety, or a weak anion moiety), or any combination thereof.

In some examples, the sorptive material may include hydrophilic-lipophilic-balance particles, such as particles comprising the copolymerization polymer product of N-vinylpyrrolidinone and divinylbenzene.

In particular examples, the fluorocarbon polymer may be a copolymer of tetrafluoroethylene and 2,2-bistrifluoromethyl-4,5-difluoro-1,3-dioxole in the ratio of 13:87; and the sorptive material may include hydrophilic-lipophilic-balance particles comprising the copolymerization polymer product of N-vinylpyrrolidinone and divinylbenzene.

The solvent may be perfluorohexane, perfluoro(2-butyl-tetrahydrofurane), perfluorotripentylamine, or any combination thereof.

In another aspect, the present disclosure provides a method of solid-phase micro-extraction (SPME), where the method includes exposing an extraction coating as discussed above to a sample matrix that includes at least one analyte; and desorbing the extracted analyte.

The desorbing may include exposing the SPME coating to a thermal-assisted desorption temperature, such as a temperature up to 300° C., and the method optionally further comprises gas chromatography or direct coupling to a spectroscopic technique suitable for detection of a thermally stable analyte, such as mass spectrometry.

The desorbing may include exposing the SPME coating to a solvent-assisted desorption solvent, and the method optionally further comprises liquid chromatography, gas chromatograph, capillary electrophoresis, or any spectroscopic technique suitable for determination of a solvent stable analyte.

The desorption may include electrothermal vaporization, arc and spark ablation, laser ablation, glow discharge, matrix-assisted laser desorption/ionization (MALDI), or desorption electrospray ionization (DESI), and the method optionally further comprises a spectroscopic technique, such as gas chromatography or direct coupling to mass spectrometry, suitable for detection of the analyte.

The analyte may be a polar compounds, such as a water-soluble compound. The analyte may be a non-polar compound. The analyte may be a non-fluorocarbon polymer.

The sample matrix may be a biological matrix or an environmental sample, such as a sludge or soil.

The SPME coating may be used more than once to extract and desorb the analyte from the sample matrix or its headspace.

BRIEF DESCRIPTION OF THE DRAWINGS

Embodiments of the present disclosure will now be described, by way of example only, with reference to the attached Figures.

DETAILED DESCRIPTION

Figure 1:
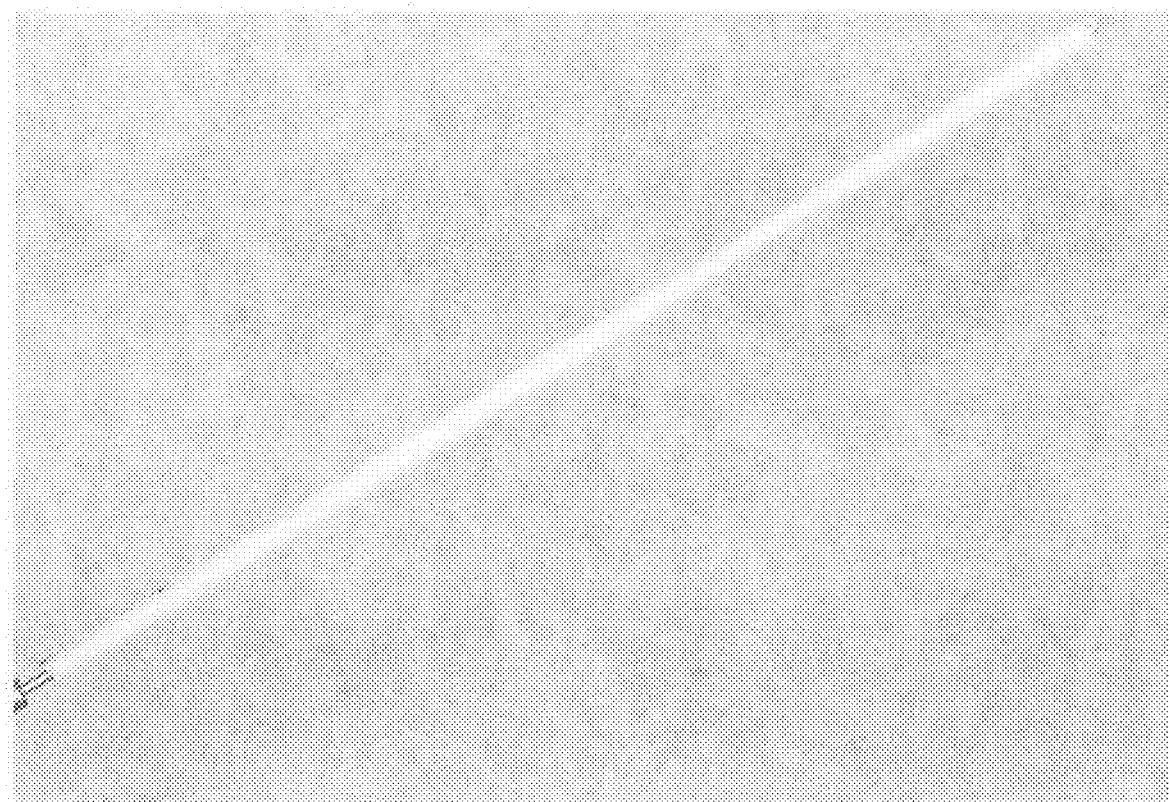
FIG. 1 is a photograph of an exemplary SPME instrument according to the present disclosure. The SPME instrument has a 90 μm thick extraction coating that includes PTFE AF2400 and HLB particles, coated on a stainless steel support shaped as a fiber.
Figure 2:
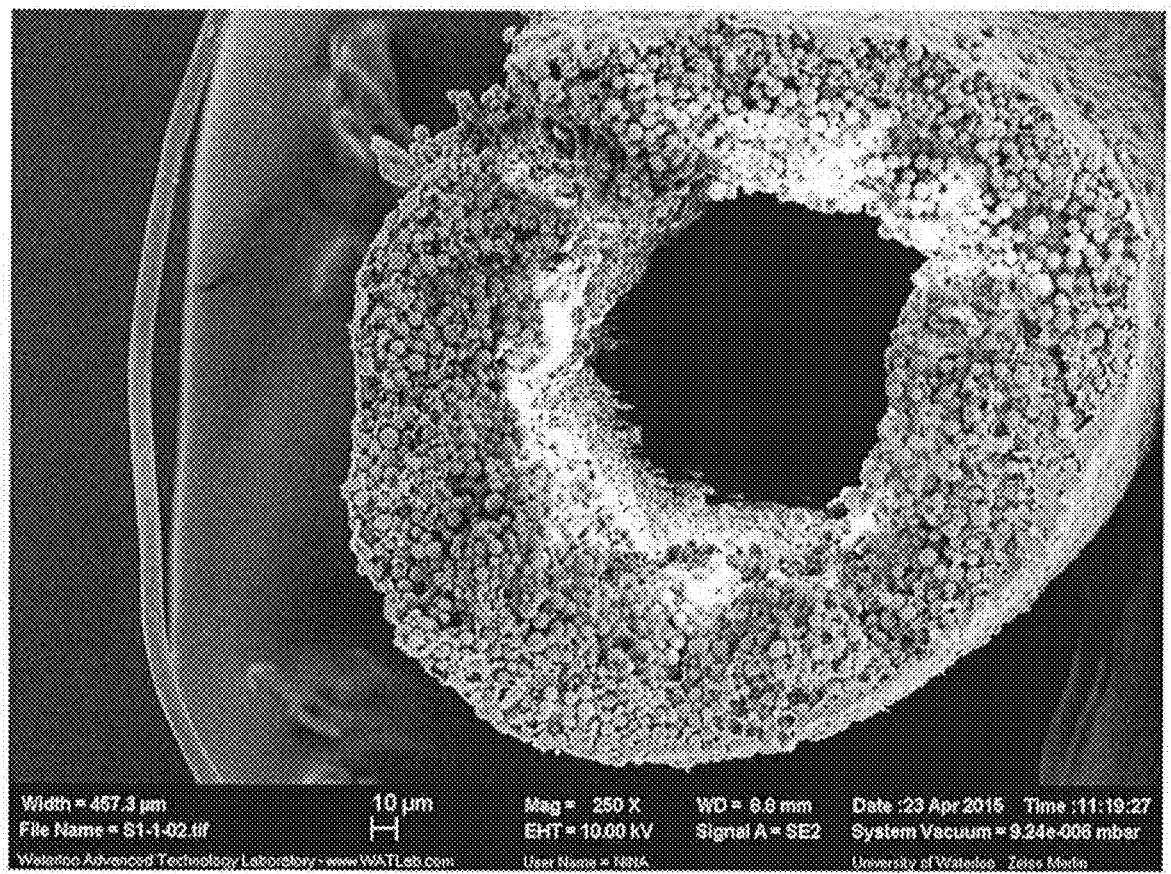
FIG. 2 is an electron micrograph image showing the cross-section of an exemplary SPME instrument according to the present disclosure. The SPME instrument has a 90 μm thick extraction coating that includes PTFE AF2400 and HLB particles.
Figure 3:
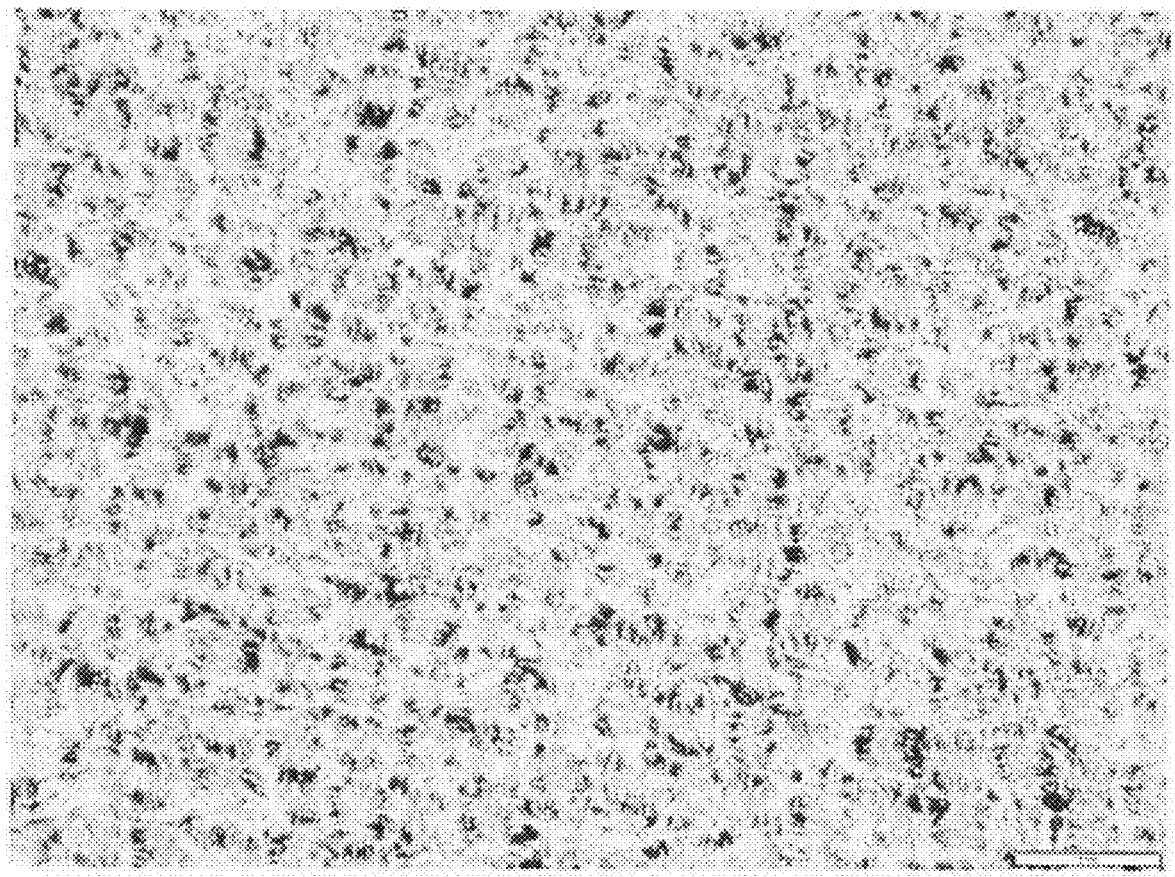
FIG. 3 is a photograph of a carbon fiber fabric coated with an extraction coating that includes PTFE AF2400 and HLB particles.
Figure 4:
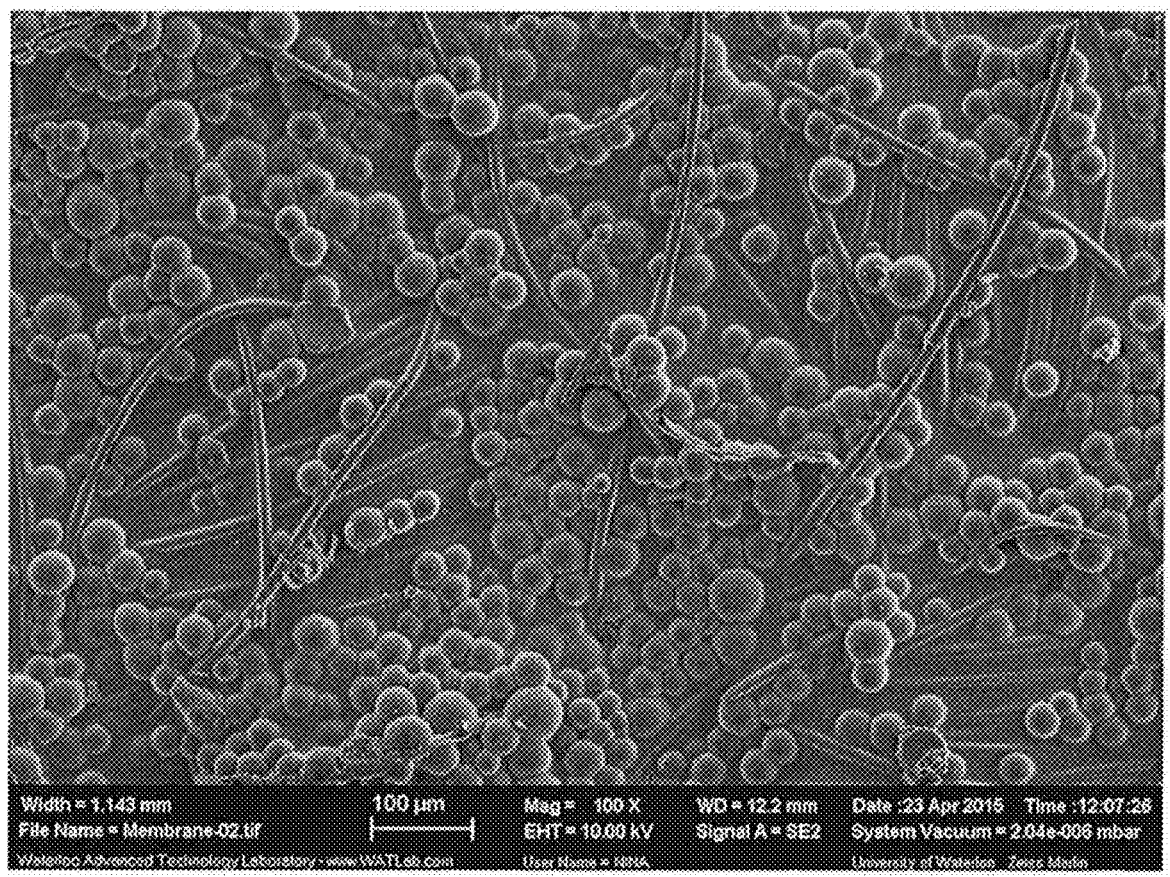
FIG. 4 is an electron micrograph image showing a 100× magnification of the coated fabric showing in FIG. 3.

Generally, the present disclosure provides an extraction coating for an SPME sampling instrument, where the extraction coating includes a particulate sorptive material immobilized in a fluorocarbon polymer that is compatible with thermal-assisted desorption techniques, solvent-assisted desorption techniques, a solid sample desorption method, or a combination thereof. The extraction coating may be referred to as "an SPME coating".

The particulate sorptive material may be material that can be used in solid phase extraction or partition chromatography (such as liquid chromatography). The particulate material may be, for example: particles, nanosheets, and/or nanotubes. As noted above, the authors of the present disclosure surprisingly determined that some exemplary fluorocarbon polymers were able to anchor particulate sorptive material to a support. Even more surprisingly, they determined that polar particulate sorptive material could be anchored to a support. The sorptive material may be adsorptive or absorptive, and may be referred to as "the adsorptive or absorptive material".

A fluorocarbon polymer according to the present disclosure refers a polymer having carbon-fluorine (C—F) bonds and carbon-hydrogen (C—H) bonds where fewer than 5% of all the C—F and C—H bonds in the fluorocarbon polymer are C—H bonds. Some particular examples of fluorocarbon polymers according to the present disclosure have substantially no C—H bonds.

Thermal- and solvent-assisted desorption techniques contemplated by the present disclosure include techniques that may be used to introduce a solid sample into an analytical instrument, such as to a gas chromatography instrument, a liquid chromatography instrument, or a capillary electrophoresis instrument.

An extraction coating that is "compatible" with a thermal-assisted desorption technique refers to a coating that loses less than 5% of its weight when exposed to the thermal desorption conditions. An extraction coating that loses less than 5% of its weight when exposed to a temperature of up to about 310° C. may be considered to be compatible with common thermal-assisted desorption techniques for SPME.

An extraction coating that is "compatible" with a solvent-assisted desorption technique refers to a coating that does not swell when exposed to a solvent or a mixture of solvents. An extraction coating that does not swell when exposed to commonly used for liquid chromatography may be considered to be compatible with common solvent-assisted desorption techniques. Exemplary solvents may have pHs from about 0.01 to about 14 and may include short chain alcohols, hydrocarbons (aliphatic, cyclic, aromatic), water, chlorinated solvents, esters, ethers, nitriles, and combinations thereof.

The extraction coating may also be compatible with one or more other well-known solid sample desorption methods, such as: electrothermal vaporization, arc and spark ablation, laser ablation, glow discharge, matrix-assisted laser desorption/ionization (MALDI), or desorption electrospray ionization (DESI). An extraction coating that is "compatible" with one of these methods refers to a coating that releases the extracted analyte efficiently with the application of the method.

The fluorocarbon polymer may be selected based on a desired stability for a desorption method, a desired biocompatibility with a sample matrix, desired immobilization characteristics for the adsorptive or absorptive material, or any combination thereof. The fluorocarbon polymer may include a polymer formed from the polymerization of a fluorocarbon monomer or of a mixture of monomers that include a fluorocarbon monomer. The monomer may be, for example: vinyl fluoride (VF1), vinylidene fluoride (VDF), tetrafluoroethylene (TFE), hexafluoropropylene (HFP), perfluoropropylvinylether (PPVE), perfluoromethylvinylether (PMVE), or chlorotrifluoroethylene (CTFE). The mixture of monomers may include, for example: VF1, VDF, TFE, HFP, PPVE, PMVE, CTFE, or any combination thereof, and may optionally include ethylene (E) and/or propylene (P) so long as fewer than 5% of all the C—F and C—H bonds in the fluorocarbon polymer are C—H bonds, In particular examples, the fluorocarbon polymer may be a polymer of, or a copolymer that includes: polytetrafluoroethylene (PTFE), fluorinated ethylene-propylene (FPE, tradename Teflon®), fluoroelastomer [tetrafluoroethylene-propylene] (FEPM, tradename AFLAS®), or any combination thereof. For example, the fluorocarbon polymer may be a Teflon Amorphous Fluoroplastic (Teflon AF) formulation, such as Teflon AF 2400 (which has a Tg of 240° C., and is also referred to as PTFE AF2400), or Teflon AF 1600 (which has a Tg of 160° C., and is also referred to as PTFE AF1600). PTFE AF 2400 is a copolymer of tetrafluoroethylene (13%) and 2,2-bistrifluorornethyl-4,5-difluoro-1,3-dioxole (87%). PTFE AF 1600 is a copolymer of tetrafluoroethylene (35%) and 2,2-bistrifluoromethyl-4,5-difluoro-1,3-dioxole (65%). These exemplary fluorocarbon polymers are particularly beneficial, in comparison to non-fluorocarbon polymers, when it is desirable to reduce or avoid the possibility that sample matrix will stick to the extraction coating.

The adsorptive or absorptive material may be selected based on the features of the intended analyte being extracted, and the intended desorption strategy. The adsorptive or absorptive material may be considered an extractive material in that it adsorbs or absorbs analytes for extraction and removal from the sample matrix. In some examples, the sorptive material may be a porous material having mesa- macro- or micro-pores. In some examples, the pores may have diameters from about 10 Å to about 10,000 Å. Such pores allow the analyte to be extracted onto or into the adsorptive or absorptive material. The pores may preferably be from about 100 Å to about 180 Å. These pore sizes provide sufficient surface area to adsorb or absorb enough analytes to be detectable, while also being an appropriate size to allow desorption so that micro-condensation is reduced or avoided. Larger pore sizes may be desirable when the target analyte is a large biomolecule, such as a protein or a peptide. The surface area of the particulate sorptive material may be from about 10 $m^2/g$ to about 3000 $m^2/g$. For example, the surface area of hydrophilic-lipophilic-balance (HLB) particles may be, from about 200 $m^2/g$ to about 800 $m^2/g$, while the surface area of carbon nanotubes and nanosheets may be up to 3000 $m^2/g$.

The adsorptive or absorptive material may be particles, nanosheets, and/or nanotubes that are suspended in the fluorocarbon polymer. Particles which may be used in coatings according to the present disclosure may be from about 1 nm to about 20 μm in diameter. Preferably, the particles may be from about 2 μm to about 20 μm in diameter, and more preferably from about 3 μm to about 10 μm in diameter. Even more preferably, the particles may be from about 3 μm to about 7 μm in diameter. Particles from about 3 μm to about 7 μm in diameter may be particularly useful as smaller sized particles have less of an effect on coating thickness and coating homogeneity than larger particles. Depending on the thickness of the coating and the relative size differences between the particles, using smaller particles may result in a coating that is more uniform in thickness and has a more homogeneous particle distribution than a coating made with larger particles. A "uniform thickness" should be understood to refer to a thickness that varies by less than 5% over the support surface. The particles may be spherical, or substantially spherical. Nanosheets which may be used in coatings according to the present disclosure may be about 1 nm to about 100 nm in thickness. Nanotubes which may be used in coatings according to the present disclosure may have a diameter from about 1 nm to about 10 nm. Preferably, the nanotubes have a diameter from about 4 nm to about 6 nm.

With some adsorptive or absorptive material, a homogeneous coating surface may be obtained when the largest dimension of the adsorptive material is less than about half the thickness of the coating. In the context of the present disclosure a "homogeneous coating surface" should be understood to refer to a coating surface having a substantially uniform distribution of the adsorptive or absorptive material and the fluorocarbon polymer on the support surface.

The adsorptive or absorptive material may be selected based on its compatibility with the intended desorption method. The adsorptive or absorptive material may be inorganic (for example a silica-based material or a metal oxide-based material), organic (for example a carbon-, carboxen- or divinylbenzene-based material), an inorganic/organic hybrid (for example a silica and organic polymer), or a mixture of inorganic and organic materials. In particular examples, the adsorptive or absorptive material may be: normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balance (HLB) particles, carboxen 1006 particles, carbowax particles, divinylbenzene (DVB) particles, octadecylsilane particles, nanoparticles, processed mineral based particles, carbon nanotubes, functionalized-carbon nanotubes, graphene, graphene oxide, functionalized-graphene, quantum dots, or any combination thereof. The functionalized-carbon nanotubes and functionalized-graphene may be functionalized with a polar or non-polar functionality. The polar functionality may be ionic. The functional group may be used to tune the extraction capability of the adsorptive or absorptive material towards a targeted compound, or a targeted class of compounds. For example, a cationic compound may be targeted for extraction by using an anionic-functionalized-carbon nanotube. HLB particles may have a specific surface area from about 700 $m^2/g$ to about 900 $m^2/g$; average pore diameters from about 70 angstroms to about 90 angstroms; total pore volumes from about 1.15 $cm^3/g$ to about 1.45 $cm^3/g$; and/or an average particle diameter from about 5.2 to about 5.7 µm. An exemplary HLB particle is made by Waters and sold under the trade name Oasis HLB. The Oasis HLB particles are made from copolymerization of two monomers, the hydrophilic N-vinylpyrrolidinone and the lipophilic divinylbenzene. The resulting HLB particles include both hydrophilic groups and lipophilic groups, and have a specific surface area of about 762 $m^2/g$, an average pore diameter of about 79 angstroms, a total pore volume of about 1.18 $cm^3/g$ and an average particle diameter of about 5.47 µm.

Although any of the above adsorptive or absorptive materials may be used for disposable coatings, some adsorptive or absorptive materials are suitable for use in coatings that are used more than once. For example, organic or inorganic polymeric particles functionalized by organic moieties (such as carbon chains from C-1 to C-30, strong and weak cation moieties, or strong and weak anion moieties) may be used more than once in solvent-assisted desorption methods. In other examples, carbon based sorbents, inorganic sorbents, divinylbenzene-based particles, and hydrophilic-lipophilic-balance particles may be used more than once with thermal- and/or solvent-assisted desorption methods.

The extraction coating may be loaded with a standard prior to exaction of any analytes of interest from the sample matrix. The internal standard may help to account for variations in the sample preparation, coating thickness, instrument response, extraction conditions, desorption of the extracted analyte, ionization of the desorbed analyte, or any combination thereof. The internal standard may be loaded on the extraction coating by exposing the coating to a known concentration (for example 50.0 µg/L) of a known compound (for example codeine-$D_3$, 6-acetylmorphine-$D_3$, or cocaine-$D_3$).

In another aspect, the present disclosure provides a SPME sampling instrument that includes a support, and an extraction coating covering at least a portion of the support, where the extraction coating is as discussed above.

The support may be formed from any acceptable material that would be amenable for the deposition of the SPME coating, and capable of being used with an intended matrix. The SPME sampling instrument may use a different support for matrices of different natures or viscosities. The support may include, for example: a metal, a metal alloy, fused silica, a polymer (e.g. polybutylene terephthalate), a plastic, a fluoro-plastic, glass wool fibers, or a carbon material (e.g. a carbon fiber fabric). The fabric may have a unit weight of about 100 $g/m^2$ to about 300 $g/m^2$. The fabric may have a thickness of about 400 to about 900 microns. The metal or metal alloy may be, for example: stainless steel, titanium, a nickel-titanium alloy, or any other metal or metal alloy known to a person of skill in the art. In particular examples, the support may be a flexible, inert, biocompatible nickel-titanium alloy, such as Nitinol. The support may be, for example, a metal with shape memory properties that enable the metal to maintain straightness, even after being inserted into tissue or being use in high-speed agitation. Nitinol is an example of a metal alloy with shape memory properties. The geometry of the support may be selected based on the sample matrix to be analyzed, the desorption technique to be used, or both. For example, a support that is to be used as a probe into a tissue, such as an in vivo tissue, may be shaped in the form of a needle or a blade, using a metal or metal alloy. In comparison to a probe having a large, blunt geometry, a needle-like support would facilitate insertion of the sampling instrument into the tissue while reducing the invasiveness of the sampling instrument. In another example, a support that is to be used as a probe in a liquid sample (such as a urine test for banned doping agents) may be shaped in the form of a carbon mesh fabric, a metallic mesh, a blade, or a thin-film. Such a support would increase the surface area available for extraction, which may result in a better detection limit.

Homogenous coating surfaces may be from about 2 µm to about 1000 µm in thickness. Coatings of this thickness may provide a suitable balance between the total amount of analyte capable of being adsorbed by the coating, and the speed and efficiency of extraction and desorption (which is based on the thickness of the extraction coating). Coating thickness may be selected based on the intended application for the sampling instrument.

In yet another aspect, the present disclosure provides a method of making an SPME sampling instrument. In some examples, the method includes mixing a fluorocarbon polymer and a sorptive material in a solvent; applying the mixture to a support to form a substantially uniform SPME coating layer; and removing the solvent. Methods where the fluorocarbon polymer is dissolved in a solvent, and the solvent is removed to leave a solid fluorocarbon polymer may be beneficial in situations where it is desirable to avoid thermal curing (such as when it is desirable to avoid in situ polymerization methods, in situations where the adsorptive or absorptive material includes chemical functionalities that could react with a monomer, or both).

Mixing the fluorocarbon polymer, the sorptive material, and the solvent may be performed in any order, or may be mixed all together at the same time. For example, the fluorocarbon polymer may be mixed with the solvent, followed by mixing the sorptive material; or the fluorocarbon polymer may be mixed with the sorptive material, following by mixing with the solvent; or the solvent and the sorptive material may be mixed together, followed by mixing the fluorocarbon polymer.

The fluorocarbon polymer may be dissolved in the solvent, such as a fluorocarbon-based fluid or a mixture that includes a fluorocarbon-based fluid. Examples of fluorocarbon-based fluids include; perfluorohexane (tradename Fluorinert™ FC-72), perfluoro(2-butyl-tetrahydrofurane) (tradename Fluorinert™ FC-75), and perfluorotripentylamine (tradename Fluorinert™ FC-70). FC-72 has a boiling point of 56° C. and may be selected for methods where it is desirable to coat the support rapidly and it is desirable to avoid thermal conditioning. FC-75 has a higher boiling point and slower evaporation rate, and may be selected for methods where it is desirable to coat the support more slowly since the coating slurry will be at substantially the same viscosity during the whole coating procedure. Thermal conditioning may be used to help remove higher boiling fluorocarbon-based fluids.

Fluorocarbon polymers are preferentially soluble in fluorocarbon-based fluids. Adding an additional solvent, such as a halogenated solvent, to the fluorocarbon-based fluid may reduce the solubility of the fluorocarbon polymer, or may generate an emulsion that may act as a porogen. Including a porogen in the solvent may be used to change the permeability of the dried fluorocarbon polymer and change the selectivity of extraction for a class of compounds. For example, FC-72, FC-75, FC-70, or any combination thereof may further include a perfluoro-polyether, such as Krytox 157-FSH (DuPont, average molecular weight of about 7,000-7,500 g/mol). Krytox 157-FSH can act as a porogen, generating pores in the dried fluorocarbon polymer that more preferentially allow certain classes of compounds (for example: pyridines) to be extracted from the sample matrix. The Krytox 157-FSH emulsion remains a part of the coating as the fluorocarbon-based fluid is evaporated, but is subsequently removed since it does not react with the polymer or the adherent material. Once removed, it leaves behind pores in the fluorocarbon polymer.

The fluorocarbon polymer may be dissolved in the solvent at a weight percentage of about 1% to about 20% wt/wt. In particular examples, the weight percentage may be about 2.6 wt % fluorocarbon polymer to solvent. Using about 2.6 wt % fluorocarbon polymer to solvent allows for both coating robustness and homogeneity.

In particular examples, the SPME coating may be prepared by covering a solid substrate with a suspension of adsorptive or absorptive particles (e.g. C-18/silica, divinylbenzene, carboxen 1006, or HLB), nanosheets (e.g. graphene, graphene oxide, or mesoporous carbon) or nanotubes (e.g. carbon nanotubes) in a solution of fluorocarbon polymer (e.g. PTFE, FPE, or FEPM) dissolved in fluorocarbon solvent (e.g. FC-72, FC-70, or FC-75).

In more particular examples, the fluorocarbon polymer is PTFE, such as PTFE AF 2400. When using PTFE AF 2400 and adsorptive or absorptive particles, such as HLB particles, the PTFE AF 2400 and the adsorptive or absorptive particles may be applied to the substrate in a ratio from about 0.5:1 to about 2:1 (w/w) based on the weight of the PTFE AF 2400 and the adsorptive or absorptive particles before dissolution in a solvent. More preferably, the PTFE AF 2400 and the adsorptive or absorptive particles are in a ratio of about 1:1 (w/w). The PTFE AF 2400 may be mixed with sufficient solvent to result in a ratio of about 1:100 to about 4:100 (w/w) of PTFE AF 2400 to solvent. More preferably, the ratio of PTFE AF 2400 to solvent is from about 2:100 to about 3:100 (w/w). Even more preferably, the PTFE AF 2400 and solvent may be mixed to form a solution of about 2.6 wt % PTFE AF 2400. As noted above, the fluorocarbon polymer may be dissolved in a fluorocarbon-based fluid. The PTFE AF 2400 may be dissolved in FC-72, FC-75, FC-70, or any mixture thereof. Preferably, the PTFE AF 2400 is dissolved in perfluorohexane (Fluorinert™ FC-72).

The fluorocarbon polymer/sorptive material mixture may be applied to the support in any manner that results in a coating of substantially consistent thickness. For example, the mixture may be applied onto the support by: dipping, spreading, brush painting, spraying, spin coating or electrospinning. For a fabric support, a coating thickness from about 5 to about 250 micrometer may be obtained with a single layer application by controlling the speed of a bar coater (varying from 5 mm/sec to 150 mm/sec). A fabric support may be coated on both sides, for example by using two bar coater applications.

The mixture may be applied to the support in a plurality of layers, such as a sufficient number of layers to provide a desired coating thickness. Applying the mixture in a plurality of layers may result in a coating that has improved bonding to the substrate, more uniform coating thickness across the coated area, or both.

Since the fluorocarbon polymer is already polymerized before being applied to the support, it is not necessary to cure the polymer and multi-layered coatings may be produced substantially faster than in methods that require monomers to be polymerized or crosslinked. The coating is formed on the support by evaporation of the solvent. Depending on what solvent is used, the solvent may be evaporated at an elevated temperature, at a reduced pressure, through flow of a drying gas (such as nitrogen) over the mixture, by leaving the coated device for a sufficient period of time, or any combination thereof. In some examples, the solvent may be evaporated over a length of time that is from about 30 seconds to about 2 minutes. With particular solvents, the evaporation time may be about 1 minute. Perfluorohexane, for example, has a boiling point of 56° C. and a vapor pressure of 27 kPa at 25° C. and may be evaporated from the mixture if it is left at room temperature for about 1 minute.

The fluorocarbon polymer-based coating may be further coated with a biocompatible layer, such as a layer of a fluorocarbon polymer that lacks sorptive material or a non-fluorocarbon based biocompatible polymer. Examples of biocompatible non-fluorocarbon based polymers include: polyacrilonitrile, polydimethylsiloxane (PDMS), and polypyrrole (PPY). Such an additional biocompatible layer may result in the SPME coating having improved compatibility with an intended sample matrix.

In some other examples, the method of making an SPME sampling instrument includes polymerizing, on a support, a coating of a fluorocarbon-based monomer, or a mixture of monomers that includes a fluorocarbon-based monomer, around the sorptive material. The coating may be formed, for example: by mixing the monomer or mixture of monomers with the sorptive material and coating the support with the reaction mixture. The monomer may be, for example: vinyl fluoride (VF1), vinylidene fluoride (VDF), tetrafluoroethylene (TFE), hexafluoropropylene (HFP), perfluoropropylvinylether (PPVE), perfluoromethylvinylether (PMVE), or chlorotrifluoroethylene (CTFE). The mixture of monomers may include, for example: VF1, VDF, TFE, HFP, PPVE, PMVE, CTFE, or any combination thereof, and may optionally include ethylene (E) and/or propylene (P) so long as fewer than 5% of all the C—F and C—H bonds in the fluorocarbon polymer are C—H bonds.

Methods of making an SPME sampling instrument may additionally include one or more support processing steps. A support processing step may: clean a surface of the support, roughen a surface of the support, or both, where the processed surface is a surface to be coated with the SPME coating. A support processing step may improve attachment of at least a portion of the SPME coating to the support. Processing the support material may include cleaning the support by sonication in water, an organic solvent, or a mixture thereof. The organic solvent may be, for example: methanol, acetonitrile, isopropyl alcohol, or any mixture thereof. Roughening the surface to be coated may include: using an abrasive (such as sand paper or any other type of sanding device), etching in hydrochloric acid (for example for 5 to 60 min) if the support material includes a metallic substrate, or applying a voltage across the support (for example for 30 seconds at a voltage of 3.5 V in a solution of water saturated with sodium chloride) if the support material includes a metallic substrate. After a roughening step, the substrate may additionally be cleaned before being coated with the SPME coating. The cleaning may include sonication in a solution of water and methanol 50:50 (v/v) for 10 minutes.

In still another aspect, the present disclosure provides a method of extracting an analyte from a sample. The method includes exposing an SPME sampling instrument according to the present disclosure to the analyte. As discussed above, the SPME sampling includes an extraction coating covering at least a portion of the support. Exposing the SPME sampling instrument to the analyte may include contacting the sample with the extraction coating, or placing the extraction coating in a headspace sufficiently close to the sample. The sampling may be, for example, in vitro or in vivo sampling. Contacting the sample with the extraction coating may include immersing the extraction coating in a sample fluid, or penetrating the extraction coating into a viscous or solid sample.

The method may optionally include rinsing the extraction coating after extracting the analyte from the sample. The rinsing may be performed with an aqueous solvent, or a mixture of aqueous and organic solvents. The rinsing may be performed under static or agitating conditions. The rinsing may reduce, during a subsequent analyte detection step, interferences due to loosely attached matrix components on the coating.

The analyte may be desorbed directly from the coating to an analytical instrument for detection, such as by mass spectrometry. Alternatively, the method may also include desorbing the analyte from the extraction coating, such as via a thermal- or solvent-based desorption, and separating the desorbed analytes by gas- or liquid-chromatography prior to detection. Thermal-base desorption may include exposure of the coating to a temperature of up to 300° C., such as about 250° C. Solvent-based desorption may include exposure of the coating to a solvent that would extract the analyte from the coating, without dissolving or swelling the coating polymer. Examples of suitable solvents may have pHs from about 0.01 to about 14 and may include short chain alcohols, hydrocarbons (aliphatic, cyclic, aromatic), water, chlorinated solvents, esters, ethers, nitriles, and combinations thereof.

The method may be implemented as part of a high-throughput automated sample preparation method.

An SPME coating according to the present disclosure may be used for direct microextraction of biological molecules (such as proteins or peptides) or small molecules from a biological, environmental, or food matrix, such as fluids and tissues. The small molecules may be hydrophobic or hydrophilic, and should preferably weigh less than 10,000 atomic mass units. Examples of such small molecules include contaminants, drugs, biomarkers and metabolites.

EXAMPLES

Example 1

SPME Sampling Fiber Prepared by Multiple Dipping Cycles

Stainless steel wires of 200 μm diameter were etched by immersion in a solution of water saturated with sodium chloride and application of a voltage of 3.5 V. Before the coating procedure, the etched substrate was sonicated in a solution water/methanol 50:50 (v/v) for 10 minutes. A coating slurry was prepared by suspending 60 mg of HLB particles (5 μm diameter) in 1.5 ml of a 2.6% (w/w) solution of PTFE AF 2400 in FC-72. FC-72 has a density of 1.68 g/cm$^3$. Accordingly, the slurry includes about 3.8 g of FC-72, about 0.10 g of PTFE AF 2400, and 60 mg of HLB particles. The ratio of PTFE AF 2400 to particles is 1.7:1 (w/w).

The slurry was deposited on the metallic support by dipping and slowly retracting the support from the slurry. Seven application cycles were used to prepare the extraction coating. After each cycle, the fiber was left at room temperature for 1 minute to allow solvent evaporation. The resulting extraction coating was about 1 cm in length and about 90 μm in thickness, and is shown in FIGS. 1A and 1B. The thickness of the extraction coating varies by less than 5% across the coated surface. No changes of the coating surface or morphology was observed after exposure at 250° C. for 1 hour under inert atmosphere.

Example 2

SPME Sampling Fabric Prepared by Film Application

A coating slurry was prepared as described in Example 1. A carbon mesh fabric having a unit weight of 115 g/m$^2$, a thickness of 406 microns, and a carbon content of 99%, which was not-pretreated before coating, was immobilized on the surface of a bar-coater in order to keep the fabric straight on the surface. The immobilized fabric was coated with the slurry using the film applicator at a constant spreading speed to result in a carbon mesh fabric having a thin, homogeneous coating layer thereon. The coated fabric was left to dry for a minute in order to evaporate the FC-72 solvent. The coating volume per SPME instrument is greater with the coated fabric compared to the coated wires of Example 1 and the authors of the present disclosure expect that the coated fabric will have a lower analyte detection threshold.

Example 3

Analysis of Fruit Metabolites in an Aqueous Matrix Using PTFE AF2400/HLB Fiber and GC-MS Ultrapure water was spiked with a mixture of all the GC-amenable analytes listed in Table 1, having diverse chemical functionalities and physical chemical characteristics. The water was spiked at concentrations ranging from 8.3 to 664.4 μg of compound per liter, keeping the organic solvent volume below 1% (v/v). The spiked water sample allowed for testing extraction of all the analytes simultaneously.

The samples were extracted using the SPME sampling fiber described in Example 1 by directly exposing the coating to the sample matrix for 8 hrs at a temperature of 35° C. while shaking the sample at 500 rpm.

The desorption, separation, and detection of the analytes was performed by an Agilent 6890/5973 GC-MS equipped with a GERSTEL CIS septumless PTV injector. The adsorbed analytes were thermally desorbed at 250° C. for 15 minute using ultrapure helium as a carrier gas and at a flow velocity of 1.5 ml/min. The capillary column used for the chromatographic separation was an Agilent J&W HP-5 (30 m, 0.25 mm i.d., 0.25 μm film thickness). The column temperature program was initially set at 35° C. for 6 min, ramped at 10° C./min to 140° C. then, ramped at 20° C./min to 270° C., and held at 270° C. for 2 min, resulting in a total run time of 24 min. Helium (purity level 99.999%) was used as carrier gas and its flow set at 1.2 ml/min. The mass spectrometer working conditions were: electron ionization (EI) 70 eV, mass range 50-350 m/z, ion source temperature: 230° C., quadrupole temperature: 150° C., and transfer line temperature: 280° C.

The same set of experiments and analysis was performed using an SPME sampling instrument having a DVB/Carboxen/PDMS (30 μm /50 μm) coating in order to compare extraction efficiency (fc values) at equilibrium conditions. When an SPME coating includes adsorptive particles, the adsorption mechanism of extraction requires that the extraction phase surface concentration (Se) of adsorbed analytes is considered rather than the extraction phase concentration. Therefore, the calculation of fibre coating/sample distribution constant (Kfs) for SPME adsorbents requires the determination of Se values or the knowledge of Se constants (since Se can be expressed as the ratio of amount extracted and the active surface of the fibre coating (Sa)). Since Sa is tedious to determine experimentally, a new constant, termed "fibre constant" (fc) representing the products Kfs*Sa for adsorptive materials, is alternatively used for the estimation of SPME enrichment factors at equilibrium.

The DVB/Carboxen/PDMS coating was obtained from Supelco Sigma Aldrich and had a 30 μm inner layer of carboxen embedded in PDMS and a 50 μm outer layer of DVB embedded in PDMS. These results are shown in Table 1 and confirm that the PTFE AF 2400/HLB coating prepared as discussed in Example 1 provides results that are comparable to, or superior to, those achieved using the DVB/Carboxen/PDMS coating. Moreover, superior reproducibility, expressed as relative standard deviation (RSD %), was obtained using the PTFE AF 2400/HLB coating as compared to the DVB/Carboxen/PDMS coating (Table 2). Reproducibility was measured by performing extractions for 30 min at 600 rpm and 30° C. Reproducibility was tested under pre-equilibrium conditions (30 min) because at shorter extraction times any error made on the extraction times reflects in higher errors in amount extracted. Reproducibility under equilibrium conditions does not vary with extraction time. Reproducibility was calculated by relative standard deviation for each analyte extracted, after a series of at least three replicate extractions, using the same coating.

TABLE 1

GC-MS analysis of fruit metabolites in an aqueous matrix using a PTFE AF2400/HLB coated fiber or a DVB/Carboxen/PDMS coated fiber

| Analyte | PTFE AF 2400/HLB coating | | DVB/Carboxen/PDMS coating | |
|---|---|---|---|---|
| | fc values | Standard deviation | fc values | Standard deviation |
| Benzene | 0.13 | 4.91E−02 | 0.15 | 2.02E−02 |
| 1-Pentanol | 0.04 | 1.67E−03 | 0.01 | 2.03E−03 |
| 2-Hexanone | 0.13 | 5.47E−03 | 0.04 | 1.69E−03 |
| Hexanal | 0.95 | 1.57E−02 | 0.31 | 1.13E−02 |
| Ethyl butanone | 0.47 | 3.56E−02 | 0.09 | 5.89E−03 |
| α-Pinene | 8.05 | 4.43E−01 | 3.77 | 3.05E−01 |
| Benzaldehyde | 0.35 | 1.24E−02 | 0.48 | 2.51E−02 |
| Limonene | 0.41 | 2.75E−01 | 0.79 | 4.46E−02 |
| Eucalyptol | 0.91 | 5.10E−03 | 0.20 | 1.84E−02 |
| Acetophenone | 0.39 | 1.38E−02 | 0.40 | 7.27E−03 |
| 2-Nonanone | 1.93 | 2.51E−01 | 1.55 | 2.33E−01 |
| Linalool | 0.66 | 1.20E−02 | 0.53 | 1.46E−03 |
| Nonanal | 3.57 | 2.87E−01 | 3.78 | 1.34E−01 |
| 1-Nonanol | 4.45 | 3.00E−03 | 4.51 | 6.57E−01 |
| Neral | 1.63 | 4.38E−02 | 2.96 | 2.54E−01 |
| Carvone | 0.49 | 1.22E−02 | 0.82 | 7.98E−02 |
| Geranial | 10.23 | 2.06E−01 | 45.92 | 2.21E−01 |
| 2-Undecanone | 15.72 | 5.31E+00 | 19.19 | 4.51E+00 |
| Ethyl nonanoate | 4.09 | 1.70E+00 | 5.21 | 1.68E−01 |
| Undecanal | 2.14 | 4.98E−01 | 2.03 | 1.43E−02 |
| ortho-Vanillin | 0.01 | 3.08E−03 | 0.04 | 1.45E−02 |
| 1-Undecanol | 4.53 | 1.63E−01 | 5.70 | 1.58E+00 |
| Ethyl undecanoate | 3.09 | 6.11E−01 | 4.38 | 1.65E−01 |

TABLE 2

Relative Standard Deviation (RSD %) (n = 3) obtained for the PTFE AF 2400/HLB coated fiber and DVB/Carboxen/PDMS toward extraction of the probe analytes for 30 minutes at 600 rpm and 30° C. in direct immersion mode.

| Analyte | PTFE AF 2400/HLB coating | DVB/Carboxen/PDMS |
|---|---|---|
| Benzene | 2.1 | 0.9 |
| 1-Pentanol | 5.1 | 7.2 |
| 2-Hexanone | 3.6 | 9.4 |
| Hexanal | 1.5 | 7.4 |
| Ethyl butanoate | 4.3 | 12.1 |
| α-Pinene | 10.6 | 8.7 |
| Benzaldehyde | 4.6 | 8.6 |
| Limonene | 9.8 | 14.8 |
| Eucalyptol | 2.1 | 8.6 |
| Acetophenone | 4.1 | 6.0 |
| 2-Nonanone | 0.6 | 12.3 |
| Linalool | 0.7 | 7.5 |
| Nonanal | 0.8 | 4.7 |
| 1-Nonanol | 6.7 | 8.7 |
| Neral | 0.2 | 14.4 |
| Carvone | 2.9 | 10.9 |
| Geranial | 2.6 | 8.4 |
| 2-Undecanone | 6.4 | 17.3 |
| Ethyl nonanoate | 10.2 | 15.4 |
| Undecanal | 1.3 | 15.5 |
| ortho-Vanillin | 2.6 | 11.8 |
| 1-Undecanol | 4.8 | 8.5 |
| Ethyl undecanoate | 13.5 | 14.0 |

Example 4

Analysis of Banned Drugs in an Aqueous Matrix Using PTFE AF2400/HLB Fiber and LC-MS/MS A phosphate buffer (pH 7.4) was spiked with a mixture of all the LC-amenable compounds listed in Table 3. The phosphate buffer was spiked at concentrations ranging from 0.1 and 1000.0 μg of compound per liter, keeping the organic solvent volume below 1% (v/v). Codeine-$D_3$, 6-acetylmorphine-$D_3$ and cocaine-$D_3$ were used as internal standards (IS) at a concentration of 50.0 μg/L.

Prior to extraction, the SPME sampling fiber described in Example 1 was conditioned for 15 min in 1.8 mL of ACN/MeOH/$H_2O$ (40:40:20, v/v/v) which was acidified to contain 0.1% (v/v) formic acid (FA), under agitation at 1200 rpm. The conditioning step was followed by a rapid rinsing in 1.8 mL of water for 2 seconds.

Extraction experiments were performed at 30 minutes in the spiked phosphate buffer using 1.8 mL of sample, under agitation at 1200 rpm. Following the extraction, a 2 second static washing step, employing 0.1 mL of water, was carried out.

The adsorbed analytes were desorbed from the fiber for 30 minutes, under agitation at 1200 rpm, using 0.1 mL of ACN/MeOH/$H_2O$ (40:40:20, v/v/v) acidified to contain 0.1% (v/v) formic acid.

In addition, using the abovementioned conditions, experiments were repeated three times in a same day and in three separate days in order to calculate intra-day and inter-day reproducibility. Moreover, using the same experimental conditions longer extraction time (660 min) was tested.

The extracted samples were run in an Exactive™ benchtop Orbitrap mass analyzer system (Thermo Scientific, San Jose, USA). Optimum conditions for each compound were determined by doing direct infusion of standards. Chromatographic separation of the analytes was achieved using a Discovery HS F5 column (100 mm×2.1 mm i.d., 3 μm; Supelco, Bellefonte, Pa., USA) using 0.3 mL/min flow rate in a ternary gradient elution with water (solvent A) and acetonitrile (solvent B) and methanol (solvent C), all acidified to contain 0.1% (v/v) formic acid. The elution employed the following gradient: the initial solvent was 5% B and 5% C and 90% A, and this solvent mixture used for the first 0.5 min of elution; over 6.5 min, the solvent mixture was raised to 50% B and 50% C; over the following 5 min, the solvent mixture was decreased to 25% B and increased to 75% C; this solvent mixture was maintained for 3.5 min; over 0.2 min the solvent mixture was returned to the initial solvent conditions; the initial solvent conditions were maintained for 2 min to ensure re-equilibration of the column before any subsequent analyte injection.

The injection volume for all standards and samples was 10 μL in full loop mode. The tray temperature of the autosampler was maintained at 5° C., the column oven compartment temperature was set at 35° C. Other conditions were set as follows: spray voltage=4000 V, vaporizer temperature=300° C., sheath gas=45 units, auxiliary gas=10, and capillary temperature=300° C. Data processing and acquisition was done using the software Xcalibur (2.0.7 SP1). Tables 3 and 4 present the figures of merit obtained for the investigated analytes in phosphate buffer solution.

TABLE 3

Figures of merit of the developed method by using a PTFE AF 2400/HLB coating (extraction time: 30 min. desorption time: 30 min)

| Analytes | LogP | MRPL | LOQ ng/mL | $R^2$ | Internal Standard |
|---|---|---|---|---|---|
| 6-Acetylmorphine | 0.41 | 50 | 1.0 | 0.998 | 6-acetylmorphine_d3 |
| Nikethamide | 0.33 | 100 | 1.0 | 0.998 | 6-acetylmorphine_d3 |
| Salbutamol | 0.64 | 100 | 1.0 | 0.992 | Testosterone_d3 |
| Codeine | 1.19 | 50 | 1.0 | 0.999 | 6-acetylmorphine_d3 |
| Heroin | 1.58 | 50 | 0.5 | 0.999 | Cocaine_d3 |
| Metoprolol | 1.6 | 100 | 5.0 | 0.997 | Testosterone_d3 |
| Prednisolone | 1.66 | 30 | 5.0 | 0.999 | Cortisol_d4 |
| Amphetamine | 1.76 | 100 | 0.5 | 0.998 | Codeine_d3 |
| Dexamethasone | 1.83 | 30 | 1.0 | 0.999 | Cortisol_d4 |
| Bisoprolol | 1.87 | 100 | 1.0 | 0.999 | Cocaine_d3 |
| Strychnine | 1.93 | 100 | 1.0 | 0.999 | Cocaine_d3 |
| Methamphetamine | 2.07 | 100 | 5.0 | 0.999 | Codeine_d3 |
| 6-Acetylcodeine | 2.08 | 50 | 5.0 | 0.999 | Cocaine_d3 |
| Formoterol | 2.2 | 100 | 1.0 | 0.999 | Cocaine_d3 |
| Trenbolone | 2.27 | 5 | 5.0 | 0.999 | Cortisol_d4 |
| Cocaine | 2.3 | 100 | 1.0 | 0.998 | Cocaine_d3 |
| Budesonide | 2.42 | 30 | 0.5 | 0.999 | Testosterone_d3 |
| Clenbuterol | 2.94 | 0.2 | 1.0 | 0.996 | 6-acetylmorphine_d3 |
| Testosterone | 3.32 | 5 | 1.0 | 0.999 | Testosterone_d3 |
| Propranolol | 3.48 | 100 | 5.0 | 0.999 | Cocaine_d3 |
| Exemestane | 3.7 | 20 | 1.0 | 0.999 | Testosterone_d3 |
| Stanozolol | 3.81 | 2 | 5.0 | 0.998 | 11-or-9-carboxy-D-THC_d3 |
| 11-nor-9-carboxy-D-THC | 5.14 | 2 | 0.5 | 0.998 | 11-or-9-carboxy-D-THC_d3 |

TABLE 4

Recoveries and reproducibility of the method discussed in Example 4 using a PTFE AF 2400/HLB coating

| | Recovery % | | | | Intra-fiber | inter-fiber |
|---|---|---|---|---|---|---|
| | 30 min | | 660 min | | reproducibility | reproducibility |
| Analytes | Avg | SD | Avg | SD | RSD % (N: 3) | RSD % (N: 3) |
| 6-Acetylmorphine | 0.3 | 0.0 | 1.0 | 0.1 | 11 | 2 |
| Nikethamide | 0.2 | 0.0 | 0.8 | 0.1 | 15 | 3 |

TABLE 4-continued

Recoveries and reproducibility of the method discussed in
Example 4 using a PTFE AF 2400/HLB coating

| Analytes | Recovery % 30 min Avg | SD | Recovery % 660 min Avg | SD | Intra-fiber reproducibility RSD % (N: 3) | inter-fiber reproducibility RSD % (N: 3) |
|---|---|---|---|---|---|---|
| Salbutamol | 0.1 | 0.0 | 0.2 | 0.0 | 1 | 14 |
| Codeine | 0.2 | 0.0 | 0.7 | 0.1 | 12 | 2 |
| Heroin | 0.5 | 0.0 | 1.7 | 0.2 | 8 | 9 |
| Metoprolol | 0.5 | 0.1 | 1.6 | 0.2 | 10 | 6 |
| Prednisolone | 0.4 | 0.0 | 1.6 | 0.2 | 7 | 6 |
| Amphetamine | 0.2 | 0.0 | 0.7 | 0.1 | 11 | 23 |
| Dexamethasone | 0.6 | 0.1 | 2.6 | 0.3 | 6 | 10 |
| Bisoprolol | 0.6 | 0.0 | 2.2 | 0.3 | 9 | 2 |
| Strychnine | 0.4 | 0.0 | 1.4 | 0.1 | 12 | 5 |
| Methamphetamine | 0.2 | 0.0 | 0.9 | 0.1 | 14 | 22 |
| 6-Acetylcodeine | 0.5 | 0.0 | 1.9 | 0.0 | 6 | 7 |
| Formoterol | 0.8 | 0.0 | 2.9 | 0.2 | 8 | 2 |
| Trenbolone | 1.6 | 0.0 | 8.4 | 0.6 | 14 | 11 |
| Cocaine | 0.5 | 0.0 | 1.9 | 0.2 | 7 | 0 |
| Budesonide | 1.4 | 0.2 | 4.6 | 0.2 | 25 | 13 |
| Cienbuterol | 0.4 | 0.0 | 1.6 | 0.2 | 5 | 5 |
| Testosterone | 1.5 | 0.1 | 6.5 | 0.9 | 13 | 2 |
| Propranolol | 1.3 | 0.1 | 4.6 | 0.6 | 12 | 3 |
| Exemestane | 2.0 | 0.1 | 7.4 | 0.5 | 23 | 5 |
| 11-nor-9-carboxy-D-THC | 1.9 | 0.3 | 4.9 | 0.0 | 31 | 3 |

Example 5

Biocompatibility Assessment for LC Analysis

The biocompatibility of the SPME coating described in Example 1 was investigated in terms of inertness to biofouling. The SPME coated fiber was exposed to consecutive adsorption/rinsing/solvent desorption cycles (which is typical of the routinely applied procedures for SPME in LC applications) using blood, urine, grape juice, human serum, and saliva as model matrices. As a quality control, extraction from PBS spiked with analytes were used. Prior to exposure to the complex matrices, 3 QC extractions from the spiked PBS were performed to show the initial performance of the coatings. The fibers were then exposed to matrices for 10 extraction/desorption cycles, and were subsequently again exposed to QC extraction in PBS in order to investigate any changes of the coating performance after matrix exposure compared to the initial performance. This cycles of PBS QC extractions and matrix extractions were performed alternately for total amount of 50 matrix exposures.

Prior to extraction, fibers were pre-conditioned in 300 μL of MeOH/ACN/H$_2$O 40:40:20 v:v:v acidified to contain 0.1% FA. Following the pre-conditioning step, a short rinsing with 300 μL ultrapure water was applied under static conditions to remove traces of organic solvents. Following the rinsing, the matrixes were extracted using the SPME fibers for 30 min at 1500 rpm agitation. The sample volumes of matrix and PBS (as QC) were kept at 300 μL and 1500 μL, respectively. The fibers were subsequently rinsed for 10 sec using 1500 μL of ultrapure water at 1500 rpm agitation. The fibers were then desorbed in 100 μL of a solution MeOH/ACN/H$_2$O 40:40:20 v:v:v acidified to contain 0.1% FA. The fibers were desorbed for 30 min or 15 min, for PBS or matrix extracts, respectively. Following the first desorption, the fibers were sequentially desorbed in 300 μL of a dicloromethane/MeOH 2:1 v:v solution for 15 min at 1500 rpm agitation. In case of blood, extractions were performed at 500 rpm in an orbital shaker and subsequently 3 rinsing cycles with ultrapure water were carried out. All other steps followed the abovementioned procedure.

Extracts from the PBS samples were analyzed by LC-MS/MS for the determination of the coating performances toward extraction of the target analytes.

The coating was inspected under microscope in order to identify any deposition of matrix components on the coating surface, at the beginning of the evaluation and before every QC extraction. There was no evidence of accumulation of biofouling after the first 50 extractions, suggesting that the coating would be suitable as a reusable probe for blood and animal tissues sampling.

Repetitive extraction results obtained for each matrix are summarized in Tables 5-9 for blood, saliva, serum, urine, and grape juice, respectively. After 50 extractions in each matrix, the SPME coating substantially maintained its initial extractive properties. Although the coatings sometimes showed a difference in extraction for the coating before matrix exposure and after the 5th extraction, repetitive exposures of the coating to the matrices after the 5th extraction did not show substantive changes to the performance of the coating. This suggests that coating is conditioned with the matrix in the first five exposures.

TABLE 5

Coating extraction performances for repetitive series of extractions in blood
(NR = normalized response)

| Blood | Myclobutanyl NR | Diazepam NR | Malathion NR | Cocaine NR | Fentanyl NR |
|---|---|---|---|---|---|
| Before extraction in matrix | 1.0 (±0.0) | 1.0 (±0.0) | 1.0 (±0.0) | 1.0 (±0.0) | 1.0 (±0.0) |
| 5$^{th}$ extraction | 0.3 (±0.1) | 0.5 (±0.1) | 0.3 (±0.0) | 0.9 (±0.1) | 0.4 (±0.0) |
| 13$^{th}$ extraction | 0.4 (±0.1) | 0.6 (±0.1) | 0.4 (±0.0) | 1.1 (±0.1) | 0.5 (±0.1) |
| 22th extraction | 0.4 (±0.1) | 0.6 (±0.1) | 0.4 (±0.1) | 1.3 (±0.1) | 0.5 (±0.1) |
| 31$^{th}$ extraction | 0.4 (±0.0) | 0.7 (±0.1) | 0.4 (±0.1) | 1.5 (±0.1) | 0.6 (±0.1) |
| 40$^{th}$ extraction | 0.4 (±0.0) | 0.6 (±0.1) | 0.4 (±0.0) | 1.4 (±0.3) | 0.5 (±0.1) |
| 50$^{th}$ extraction | 0.3 (±0.1) | 0.4 (±0.1) | 0.3 (±0.1) | 1.0 (±0.3) | 0.4 (±0.1) |

TABLE 6

Coating extraction performances for repetitive series of extractions in grape juice
(NR = normalized response)

| Grape juice | Myclobutanyl NR | Diazepam NR | Malathion NR | Methadone NR | Cocaine NR | Fentanyl NR |
|---|---|---|---|---|---|---|
| Before extraction in matrix | 1.0 (±0.0) | 1.0 (±0.0) | 1.0 (±0.0) | 1.0 (±0.0) | 1.0 (±0.0) | 1.0 (±0.0) |
| 5$^{th}$ extraction | 1.1 (±0.2) | 1.1 (±0.2) | 1.1 (±0.2) | 1.2 (±0.2) | 1.6 (±0.2) | 1.2 (±0.2) |
| 13$^{th}$ extraction | 1.6 (±0.1) | 1.7 (±0.2) | 1.5 (±0.1) | 1.7 (±0.1) | 2.4 (±0.2) | 1.8 (±0.1) |
| 22$^{nd}$ extraction | 1.4 (±0.2) | 1.6 (±0.2) | 1.4 (±0.1) | 1.6 (±0.2) | 2.5 (±0.7) | 1.7 (±0.2) |
| 31$^{st}$ extraction | 1.4 (±0.1) | 1.8 (±0.1) | 1.5 (±0.0) | 1.6 (±0.0) | 2.7 (±0.3) | 1.8 (±0.0) |
| 40$^{th}$ extraction* | 1.1 | 1.6 | 1.2 | 1.4 | 2.8 | 1.6 |
| 50$^{th}$ extraction* | 1.1 | 1.6 | 1.2 | 1.5 | 3.2 | 1.7 |

*these results were obtained in duplicate, thus standard deviations could not be caculated

TABLE 7

Coating extraction performances for repetitive series of extractions in urine
(NR = normalized response)

| Urine | Myclobutanyl NR | Diazepam NR | Malathion NR | Methadone NR | Cocaine NR | Fentanyl NR |
|---|---|---|---|---|---|---|
| Before extraction in matrix | 1.0 (±0.0) | 1.0 (±0.0) | 1.0 (±0.0) | 1.0 (±0.0) | 1.0 (±0.0) | 1.0 (±0.0) |
| 5$^{th}$ extraction | 1.2 (±0.2) | 1.6 (±0.3) | 1.2 (±0.2) | 1.4 (±0.3) | 2.5 (±0.4) | 1.5 (±0.3) |
| 13$^{th}$ extraction | 1.4 (±0.1) | 1.8 (±0.1) | 1.4 (±0.2) | 1.7 (±0.1) | 3.6 (±0.2) | 1.9 (±0.2) |
| 22$^{nd}$ extraction | 1.0 (±0.0) | 1.4 (±0.1) | 1.1 (±0.1) | 1.3 (±0.1) | 2.8 (±0.1) | 1.4 (±0.0) |
| 31$^{st}$ extraction | 1.3 (±0.1) | 1.9 (±0.0) | 1.5 (±0.1) | 1.7 (±0.0) | 3.5 (±0.1) | 1.9 (±0.1) |
| 40$^{th}$ extraction | 1.5 (±0.5) | 2.2 (±0.5) | 1.7 (±0.6) | 1.9 (±0.2) | 4.3 (±0.3) | 2.2 (±0.3) |
| 50$^{th}$ extraction | 1.5 (±0.2) | 2.3 (±0.1) | 1.6 (±0.4) | 2.1 (±0.1) | 5.1 (±0.7) | 2.2 (±0.3) |

TABLE 8

Coating extraction performances for repetitive series of extractions in serum
(NR = normalized response)

| Serum | Myclobutanyl NR | Diazepam NR | Malathion NR | Diazinone NR | Cocaine NR | Fentanyl NR |
|---|---|---|---|---|---|---|
| Before extraction in matrix | 1.0 (±0.0) | 1.0 (±0.0) | 1.0 (±0.0) | 1.0 (±0.0) | 1.0 (±0.0) | 1.0 (±0.0) |
| 5$^{th}$ extraction | 0.7 (±0.1) | 1.0 (±0.2) | 0.6 (±0.1) | 0.3 (±0.1) | 2.0 (±0.3) | 0.9 (±0.2) |
| 13$^{th}$ extraction | 1.0 (±0.2) | 1.3 (±0.2) | 0.7 (±0.1) | 0.4 (±0.1) | 2.4 (±0.1) | 1.1 (±0.2) |
| 22$^{nd}$ extraction | 0.9 (±0.1) | 1.3 (±0.1) | 0.6 (±0.0) | 0.3 (±0.0) | 2.6 (±0.1) | 1.1 (±0.1) |
| 31$^{st}$ extraction | 1.2 (±0.1) | 1.6 (±0.1) | 0.8 (±0.1) | 0.5 (±0.1) | 3.1 (±0.2) | 1.5 (±0.1) |
| 40$^{th}$ extraction | 1.2 (±0.1) | 1.7 (±0.1) | 0.8 (±0.0) | 0.5 (±0.1) | 3.1 (±0.1) | 1.5 (±0.1) |
| 50$^{th}$ extraction | 0.9 (±0.0) | 1.3 (±0.1) | 0.6 (±0.0) | 0.3 (±0.0) | 2.6 (±0.2) | 1.2 (±0.1) |

TABLE 9

Coating extraction performances for repetitive series of extractions in saliva
(NR = normalized response)

| Saliva | Myclobutanyl NR | Diazepam NR | Malathion NR | Diazinone NR | Cocaine NR | Fentanyl NR |
|---|---|---|---|---|---|---|
| Before extraction in matrix | 1.0 (±0.0) | 1.0 (±0.0) | 1.0 (±0.0) | 1.0 (±0.0) | 1.0 (±0.0) | 1.0 (±0.0) |
| 5th extraction | 1.7 (±0.1) | 2.1 (±0.4) | 1.2 (±0.0) | 0.7 (±0.1) | 2.9 (±0.8) | 2.0 (±0.3) |
| 13th extraction | 2.0 (±0.4) | 2.4 (±0.7) | 1.2 (±0.2) | 0.8 (±0.1) | 3.2 (±1.3) | 2.4 (±0.8) |
| 22nd extraction | 1.9 (±0.2) | 2.3 (±0.5) | 1.2 (±0.0) | 0.7 (±0.1) | 3.8 (±0.6) | 2.4 (±0.3) |
| 31st extraction | 2.0 (±0.1) | 2.4 (±0.3) | 1.1 (±0.0) | 0.6 (±0.1) | 3.7 (±0.5) | 2.3 (±0.3) |
| 40th extraction | 2.2 (±0.4) | 2.6 (±0.8) | 1.1 (±0.1) | 0.7 (±0.1) | 3.9 (±1.3) | 2.4 (±0.7) |

Example 6

Absolute Matrix Effect Assessment

The biocompatibility of the SPME coating described in Example 1 was investigated in terms of its capability to avoid co-extraction of matrix components that may contribute to ion suppression or enhancement in LC-ESI-MS analysis. The SPME coating was investigated in terms of absolute matrix effect assessment using whole blood, grape juice, saliva, human serum, and urine as sample matrices.

Ion suppression or enhancement resulting from co-eluting constituents was investigated using nicotine, cocaine, diazepam, malathion, myclobutanyl, diazinon, fentanyl, and methadone, which are compounds that possess a wide range of polarities, as target analytes.

Prior to extraction, fibers were pre-conditioned in 500 µL of MeOH/ACN/H$_2$O 40:40:20 v:v:v acidified to contain 0.1% FA. Following the pre-conditioning step, a short rinsing with 300 µL ultrapure water was applied under static conditions to remove traces of organic solvents. Exactions were performed for 30 min in 500 µL of sample matrix. Following extraction, the fibers were rinsed with 1.5 mL of ultrapure water for 10 second. After the rinsing step, the extracted analytes were desorbed for 30 min in 500 µL of ACN/MeOH/Water (40:40:20, v/v/v), acidified to contain 0.1% formic acid. The first desorption solution was preserved for absolute matrix effect investigation. The fiber was subjected to a second desorption step, performed using 500 µL dichloromethane/MeOH 2:1 v:v for 15 min. All steps were performed at 850 rpm agitation using manual Concept 96 system.

For the testing using whole blood, the fibers were treated with a pre-conditioning step prior to extraction. The fibers were pre-conditioned for 30 min in 500 µL of ACN/MeOH/Water 40:40:20 v:v:v, acidified to contain 0.1% formic acid. Following the pre-conditioning step, the fibers were washed for 10 seconds with ultrapure water in order to remove traces of organic solvent from the coating surface. Exactions were performed in an orbital shaker at 500 rpm for 30 min in 500 µL of sample matrix. After extraction, three sequential washing steps were performed using 500 µL ultrapure water for 10 second in a vortexer. After the third washing step, the analytes were desorbed for 30 min in 500 µL of ACN/MeOH/Water 40:40:20 v:v:v, acidified to contain 0.1% formic acid. The first desorption solution was preserved for absolute matrix effect investigation. Following the first desorption step, the fiber was subjected to a second desorption step, performed using 500 µL dichloromethane/MeOH 2:1 v:v for 15 min. The conditioning, first washing, and two desorption steps were all performed in mechanical agitator.

The above-mentioned procedures were repeated 50 times for each matrix in order to investigate the cumulative effect of any possible matrix constituent deposition and consequential absolute matrix effect.

Afterwards, the extracts were spiked to contain 10 or 100 ng/mL of nicotine, cocaine, diazepam, malathion, myclobutanyl, diazinon, fentanyl, and methadone. In parallel, as controls, aliquots of neat desorption solvents were also spiked to contain 10 or 100 ng/mL of the mixed analytes. Spiked matrix extracts and spiked neat solvents were injected to LC-MS/MS instrument and ratio of (i) the response of peak area of each analyte in the spiked extract to (ii) the response of peak area of each analyte in the spiked neat solvent, was used to calculated absolute matrix effect for each analyte.

The absolute matrix effects for each tested analyte are provided in Tables 10 to 25. The Teflon-HLB fibers discussed in Example 1 provided good matrix compatibility for all the matrices tested.

TABLE 10

Absolute matrix effect on 10 ng/mL nicotine (logP 0.87) extracted from various matrices

| Nicotine (10 ng/mL) | Blood | Grape Juice | Saliva | Serum | Urine |
|---|---|---|---|---|---|
| 1st | 103 (±7) | 103 (±8) | 130 (±2) | 95 (±4) | 101 (±4) |
| 10th | 100 (±5) | 94 (±6) | 123 (±5) | 100 (±4) | 99 (±5) |
| 20th | 102 (±6) | 101 (±5) | 125 (±5) | 102 (±4) | 100 (±4) |
| 30th | 101 (±6) | 101 (±6) | 130 (±5) | 103 (±3) | 99 (±6) |
| 40th | 96 (±6) | 98 (±5) | 130 (±5) | 96 (±3) | 101 (±6) |
| 50th | 98 (±6) | 97 (±5) | 124 (±22) | 103 (±6) | 103 (±6) |

TABLE 11

Absolute matrix effect on 100 ng/mL nicotine (logP 0.87) extracted from various matrices

| Nicotine (10 ng/mL) | Blood | Grape Juice | Saliva | Serum | Urine |
|---|---|---|---|---|---|
| 1st | 98 (±4) | 96 (±6) | 99 (±3) | 96 | 106 (±5) |
| 10th | 97 (±4) | 103 (±5) | 103 (±3) | 103 (±4) | 113 (±4) |
| 20th | 102 (±5) | 100 (±4) | 101 (±8) | 100 (±3) | 114 (±4) |
| 30th | 101 (±4) | 100 (±6) | 106 (±2) | 102 (±3) | 114 (±3) |
| 40th | 97 (±5) | 101 (±5) | 104 (±6) | 100 (±3) | 112 (±5) |
| 50th | 100 (±5) | 104 (±6) | 102 (±2) | 101 (±3) | 125 (±3) |

TABLE 12

Absolute matrix effect on 10 ng/mL cocaine (logP 1.97) extracted from various matrices

| Cocaine (10 ng/mL) | Blood | Grape Juice | Saliva | Serum | Urine |
|---|---|---|---|---|---|
| 1st | 101 (±4) | 106 (±7) | 124 (±9) | 98 (±5) | 101 (±5) |
| 10th | 100 (±6) | 93 (±5) | 114 (±5) | 96 (±3) | 95 (44) |
| 20th | 104 (±7) | 99 (±10) | 112 (±6) | 101 (±5) | 98 (±4) |
| 30th | 98 (±6) | 101 (±5) | 114 (±3) | 100 (±3) | 97 (±5) |
| 40th | 92 (±7) | 102 (±3) | 118 (±5) | 96 (±3) | 96 (5) |
| 50th | 95 (±7) | 103 (±4) | 112 (±10) | 102 (±5) | 99 (±5) |

TABLE 13

Absolute matrix effect on 100 ng/mL cocaine (logP 1.97) extracted from various matrices

| Cocaine (100 ng/mL) | Blood | Grape Juice | Saliva | Serum | Urine |
|---|---|---|---|---|---|
| 1st | 98 (±6) | 100 (±5) | 98 (±3) | 95 | 106 (±5) |
| 10th | 99 (±5) | 106 (±6) | 102 (±3) | 106 (±5) | 115 (±6) |
| 20th | 104 (±5) | 102 (±5) | 95 (±7) | 104 (±5) | 116 (±5) |
| 30th | 100 (±6) | 102 (±6) | 101 (±3) | 106 (±6) | 112 (±4) |
| 40th | 98 (±5) | 102 (±4) | 104 (±5) | 103 (±6) | 109 (±7) |
| 50th | 101 (±4) | 106 (±3) | 101 (±4) | 103 (±6) | 122 (±4) |

TABLE 14

Absolute matrix effect on 10 ng/ml diazepam (logP 2.6) extracted from various matrices

| Diazepam (10 ng/mL) | Blood | Grape Juice | Saliva | Serum | Urine |
|---|---|---|---|---|---|
| 1st | 93 (±7) | 106 (±7) | 113 (±2) | 93 (±3) | 91 (±6) |
| 10th | 93 (±7) | 93 (±5) | 111 (±6) | 95 (±5) | 87 (±6) |
| 20th | 97 (±5) | 95 (±5) | 110 (±4) | 97 (±5) | 88 (±6) |
| 30th | 94 (±6) | 95 (±6) | 114 (±3) | 98 (±6) | 92 (±7) |
| 40th | 91 (±8) | 100 (±4) | 115 (±5) | 93 (±5) | 90 (±6) |
| 50th | 93 (±8) | 97 (±5) | 105 (±13) | 97 (±5) | 90 (±7) |

TABLE 15

Absolute matrix effect on 100 ng/mL diazepam (logP 2.6) extracted from various matrices

| Diazepam (100 ng/mL) | Blood | Grape Juice | Saliva | Serum | Urine |
|---|---|---|---|---|---|
| 1st | 97 (±4) | 99 (±6) | 95 (±1) | 86 | 99 (±4) |
| 10th | 97 (±5) | 103 (±4) | 100 (±4) | 96 (±4) | 105 (±5) |
| 20th | 102 (±5) | 97 (±5) | 95 (±6) | 94 (±4) | 107 (±5) |
| 30th | 96 (±5) | 99 (±7) | 100 (±2) | 96 (±4) | 104 (±4) |
| 40th | 95 (±5) | 102 (±3) | 100 (±2) | 95 (±3) | 101 (±6) |
| 50th | 95 (±4) | 103 (±3) | 98 (±5) | 94 (±4) | 113 (±4) |

TABLE 16

Absolute matrix effect on 10 ng/mL malathion (logP 2.7) extracted from various matrices

| Malathion (10 ng/mL) | Blood | Grape Juice | Saliva | Serum | Urine |
|---|---|---|---|---|---|
| 1st | 98 (±5) | 99 (±9) | 99 (±7) | 95 (±8) | 104 (±8) |
| 10th | 98 (±8) | 92 (±10) | 100 (±8) | 104 (±6) | 110 (±7) |
| 20th | 109 (±11) | 100 (±11) | 98 (±8) | 104 (±10) | 110 (±7) |
| 30th | 105 (±8) | 96 (±11) | 102 (±8) | 106 (±8) | 106 (±7) |
| 40th | 105 (±27) | 97 (±10) | 95 (±7) | 102 (±7) | 103 (±10) |
| 50th | 108 (±9) | 94 (±10) | 88 (±11) | 104 (±7) | 117 (±7) |

TABLE 17

Absolute matrix effect on 100 ng/mL malathion (logP 2.7) extracted from various matrices

| Malathion (100 ng/mL) | Blood | Grape Juice | Saliva | Serum | Urine |
|---|---|---|---|---|---|
| 1st | 96 (±9) | 92 (±8) | 100 (±8) | 89 | 104 (±8) |
| 10th | 91 (±8) | 96 (±7) | 106 (±6) | 97 (±6) | 110 (±7) |
| 20th | 102 (±8) | 93 (±6) | 103 (±10) | 97 (±7) | 110 (±7) |
| 30th | 97 (±9) | 94 (±6) | 110 (±8) | 101 (±7) | 106 (±7) |
| 40th | 93 (±8) | 94 (±6) | 111 (±7) | 98 (±6) | 103 (±10) |
| 50th | 97 (±9) | 93 (±5) | 104 (±7) | 95 (±7) | 117 (±7) |

TABLE 18

Absolute matrix effect on 10 ng/mL myclobutanyl
(logP 2.9) extracted from various matrices

| Myclobutanyl (10 ng/mL) | Blood | Grape Juice | Saliva | Serum | Urine |
|---|---|---|---|---|---|
| 1st  | 98 (±8)  | 97 (±11) | 102 (±9)  | 92 (±9) | 99 (±10) |
| 10th | 97 (±7)  | 92 (±9)  | 102 (±10) | 96 (±9) | 92 (±8)  |
| 20th | 107 (±7) | 97 (±9)  | 101 (±9)  | 97 (±9) | 93 (±9)  |
| 30th | 101 (±7) | 96 (±9)  | 103 (±11) | 95 (±9) | 95 (±10) |
| 40th | 98 (±11) | 96 (±9)  | 98 (±9)   | 90 (±8) | 97 (±10) |
| 50th | 100 (±9) | 92 (±9)  | 91 (±12)  | 95 (±9) | 94 (±9)  |

TABLE 19

Absolute matrix effect on 100 ng/mL myclobutanyl
(logP 2.9) extracted from various matrices

| Myclobutanyl (100 ng/mL) | Blood | Grape Juice | Saliva | Serum | Urine |
|---|---|---|---|---|---|
| 1st  | 95 (±13)  | 96 (±8)  | 98 (±8)   | 88       | 106 (±8) |
| 10th | 93 (±10)  | 103 (±5) | 108 (±7)  | 100 (±5) | 111 (±8) |
| 20th | 101 (±10) | 101 (±6) | 103 (±9)  | 96 (±5)  | 110 (±9) |
| 30th | 96 (±10)  | 98 (±7)  | 109 (±6)  | 97 (±7)  | 109 (±6) |
| 40th | 91 (±11)  | 100 (±5) | 113 (±7)  | 96 (±5)  | 104 (±9) |
| 50th | 95 (±12)  | 98 (±4)  | 109 (±8)  | 94 (±5)  | 118 (±7) |

TABLE 20

Absolute matrix effect on 10 ng/mL diazinon
(logP 3.8) extracted from various matrices

| Diazinon (10 ng/mL) | Blood | Grape Juice | Saliva | Serum | Urine |
|---|---|---|---|---|---|
| 1st  | 99 (±5)  | 103 (±9)  | 122 (±7)  | 100 (±1) | 103 (±5) |
| 10th | 97 (±5)  | 98 (±10)  | 121 (±8)  | 101 (±4) | 100 (±7) |
| 20th | 101 (±8) | 104 (±8)  | 119 (±8)  | 102 (±5) | 100 (±7) |
| 30th | 101 (±5) | 105 (±6)  | 119 (±8)  | 104 (±4) | 97 (±5)  |
| 40th | 97 (±8)  | 102 (±6)  | 114 (±6)  | 101 (±3) | 98 (±5)  |
| 50th | 93 (±8)  | 102 (±6)  | 109 (±14) | 106 (±3) | 99 (±4)  |

TABLE 21

Absolute matrix effect on 100 ng/mL diazinon
(logP 3.8) extracted from various matrices

| Diazinon (100 ng/mL) | Blood | Grape Juice | Saliva | Serum | Urine |
|---|---|---|---|---|---|
| 1st  | 100 (±6) | 100 (±9) | 98 (±6)  | 97       | 105 (±4) |
| 10th | 101 (±8) | 106 (±5) | 103 (±5) | 103 (±5) | 116 (±3) |
| 20th | 101 (±6) | 102 (±5) | 99 (±8)  | 101 (±4) | 113 (±4) |
| 30th | 98 (±5)  | 102 (±6) | 98 (±3)  | 107 (±6) | 114 (±6) |
| 40th | 98 (±5)  | 104 (±6) | 102 (±2) | 104 (±5) | 112 (±7) |
| 50th | 101 (±5) | 108 (±6) | 99 (±3)  | 104 (±7) | 124 (±6) |

TABLE 22

Absolute matrix effect on 10 ng/mL fentanyl
(logP 4.1) extracted from various matrices

| Fentanyl (10 ng/mL) | Blood | Grape Juice | Saliva | Serum | Urine |
|---|---|---|---|---|---|
| 1st  | 96 (±3)  | 102 (±6) | 122 (±4) | 97 (±5)  | 103 (±5) |
| 10th | 95 (±5)  | 94 (±7)  | 115 (±6) | 99 (±5)  | 96 (±4)  |
| 20th | 100 (±8) | 98 (±9)  | 112 (±7) | 100 (±5) | 98 (±4)  |
| 30th | 95 (±6)  | 100 (±8) | 112 (±5) | 101 (±6) | 98 (±5)  |

TABLE 22-continued

Absolute matrix effect on 10 ng/mL fentanyl
(logP 4.1) extracted from various matrices

| Fentanyl (10 ng/mL) | Blood | Grape Juice | Saliva | Serum | Urine |
|---|---|---|---|---|---|
| 40th | 92 (±7) | 101 (±7) | 114 (±7) | 99 (±6) | 96 (±6) |
| 50th | 95 (±4) | 98 (±7) | 112 (±15) | 103 (±8) | 99 (±5) |

TABLE 23

Absolute matrix effect on 100 ng/mL fentanyl
(logP 4.1) extracted from various matrices

| Fentanyl (100 ng/mL) | Blood | Grape Juice | Saliva | Serum | Urine |
|---|---|---|---|---|---|
| 1st | 98 (±8) | 102 (±5) | 103 (±2) | 96 | 107 (±2) |
| 10th | 100 (±7) | 103 (±3) | 102 (±4) | 104 (±6) | 114 (±6) |
| 20th | 101 (±5) | 103 (±4) | 96 (±9) | 105 (±5) | 113 (±5) |
| 30th | 99 (±6) | 100 (±5) | 103 (±4) | 104 (±4) | 113 (±5) |
| 40th | 98 (±3) | 109 (±6) | 103 (±6) | 103 (±3) | 109 (±8) |
| 50th | 102 (±4) | 106 (±7) | 101 (±4) | 103 (±5) | 121 (±5) |

TABLE 24

Absolute matrix effect on 10 ng/mL methadone
(logP 4.1) extracted from various matrices

| Methadone (10 ng/mL) | Blood | Grape Juice | Saliva | Serum | Urine |
|---|---|---|---|---|---|
| 1st | 99 (±7) | 106 (±8) | 124 (±8) | 99 (±5) | 101 (±5) |
| 10th | 97 (±6) | 97 (±8) | 119 (±7) | 99 (±6) | 98 (±4) |
| 20th | 102 (±7) | 100 (±10) | 119 (±5) | 100 (±6) | 98 (±3) |
| 30th | 99 (±6) | 101 (±9) | 117 (±4) | 101 (±6) | 98 (±6) |
| 40th | 93 (±6) | 99 (±6) | 118 (±3) | 101 (±3) | 97 (±6) |
| 50th | 94 (±7) | 101 (±6) | 115 (±13) | 102 (±3) | 100 (±6) |

TABLE 25

Absolute matrix effect on 100 ng/mL methadone
(logP 4.1) extracted from various matrices

| Methadone (100 ng/mL) | Blood | Grape Juice | Saliva | Serum | Urine |
|---|---|---|---|---|---|
| 1st | 99 (±4) | 102 (±4) | 102 (±4) | 98 | 108 (±4) |
| 10th | 100 (±4) | 105 (±8) | 99 (±3) | 104 (±5) | 114 (±6) |
| 20th | 103 (±5) | 101 (±5) | 98 (±6) | 103 (±7) | 115 (±7) |
| 30th | 96 (±9) | 102 (±5) | 102 (±3) | 105 (±3) | 112 (±4) |
| 40th | 98 (±6) | 105 (±6) | 102 (±4) | 103 (±3) | 107 (±7) |
| 50th | 100 (±5) | 104 (±8) | 100 (±2) | 103 (±4) | 123 (±7) |

Example 7

Biocompatibility Assessment for GC

The capability of the SPME coating described in Example 1 was investigated in terms of its ability to maintain its extraction capability constant after extraction in complex matrixes and thermal desorption into the GC injection port. Grape juice, serum, urine and saliva were used as model matrixes.

The SPME coatings were exposed to the model matrixes for 30 minutes at 300 rpm and 35° C. The coatings were then rinsed in ultrapure water (30 sec at 500 rpm). Afterwards, desorption was performed by inserting the coating in the GC-injector port for 15 minutes at 270° C. The coatings were then washed in a mixture MeOH/H$_2$O for 1 minute at 500 rpm. This extraction/desorption procedure was repeated for up to 50 extractions. The extraction performance of the coating was evaluated by QC extractions of known concentrations of diazepam, methadone, malathion, diazinon, cocaine, and myclobutanil from a nanopure water solution. The QC extractions were performed for 30 minutes at 500 rpm and 40° C. The coating was desorbed in the GC-injector port for 15 minutes at 270° C. The QC analyses were carried out at the beginning of the evaluation, and after every ten extraction from the sample matrices. No evidence of accumulation of biofouling was observed after the first 50 extractions.

The repetitive extraction results obtained for each matrix are summarized in Tables 26-29 for grape juice, urine, saliva, and serum, respectively.

Although some residual attachment of matrix may occur on the coating surface, the tables indicate that the coating extraction capability does not drop below 80% when exposed to the exemplary matrixes. The response can be corrected by internal standard.

TABLE 26

Coating extraction performances for repetitive series of extractions in grape juice (the % extracted are relative to the amount extracted by the coating at the beginning of the evaluation)

| | Grape juice | | | | |
|---|---|---|---|---|---|
| | 10th extraction % extracted | 20th extraction % extracted | 30th extraction % extracted | 40th extraction % extracted | 50th extraction % extracted |
| Diazinon | 102 (±5) | 98 (±9) | 94 (±5) | 96 (±12) | 83 (±4) |
| Methadone | 97 (±2) | 93 (±2) | 92 (±1) | 89 (±1) | 85 (±2) |
| Malathion | 99 (±2) | 96 (±2) | 90 (±4) | 90 (±1) | 88 (±1) |
| Diazepam | 99 (±3) | 95 (±3) | 90 (±3) | 90 (±5) | 84 (±4) |
| Cocaine | 98 (±4) | 94 (±5) | 89 (±5) | 89 (±6) | 86 (±3) |
| Myclobutanil | 99 (±3) | 95 (±2) | 93 (±4) | 89 (±4) | 86 (±4) |

TABLE 27

Coating extraction performances for repetitive series of extractions in urine (the % extracted are relative to the amount extracted by the coating at the beginning of the evaluation)

| | Urine | | | | |
|---|---|---|---|---|---|
| | 10th extraction % extracted | 20th extraction % extracted | 30th extraction % extracted | 40th extraction % extracted | 50th extraction % extracted |
| Diazinon | 100 (±2) | 98 (±2) | 98 (±2) | 97 (±2) | 94 (±2) |
| Methadone | 99 (±3) | 98 (±1) | 97 (±1) | 95 (±2) | 89 (±3) |
| Malathion | 99 (±5) | 95 (±3) | 93 (±5) | 92 (±0.4) | 91 (±3) |
| Diazepam | 99 (±1) | 99 (±7) | 97 (±2) | 93 (±4) | 89 (±6) |
| Cocaine | 101 (±4) | 99 (±5) | 99 (±3) | 97 (±3) | 80 (±4) |
| Myclobutanil | 99 (±8) | 96 (±6) | 96 (±5) | 87 (±10) | 80 (±5) |

TABLE 28

Coating extraction performances for repetitive series of extractions in saliva (the % extracted are relative to the amount extracted by the coating at the beginning of the evaluation)

| | Saliva | | | | |
|---|---|---|---|---|---|
| | 10th extraction % extracted | 20th extraction % extracted | 30th extraction % extracted | 40th extraction % extracted | 50th extraction % extracted |
| Diazinon | 99 (±1) | 98 (±2) | 95 (±1) | 90 (±2) | 81 (±7) |
| Methadone | 96 (±5) | 95 (±3) | 90 (±1) | 84 (±5) | 81 (±3) |
| Malathion | 99 (±5) | 100 (±1) | 94 (±2) | 85 (±2) | 84 (±5) |
| Diazepam | 99 (±1) | 99 (±1) | 95 (±2) | 88 (±4) | 81 (±7) |
| Cocaine | 99 (±2) | 96 (±1) | 90 (±3) | 85 (±2) | 86 (±4) |
| Myclobutanil | 98 (±2) | 93 (±3) | 88 (±1) | 80 (±4) | 80 (±8) |

TABLE 29

Coating extraction performances for repetitive series of extractions in saliva (the % extracted are relative to the amount extracted by the coating at the beginning of the evaluation)

| | Serum | | | | |
|---|---|---|---|---|---|
| | 10th extraction % extracted | 20th extraction % extracted | 30th extraction % extracted | 40th extraction % extracted | 50th extraction % extracted |
| Diazinon | 100 (±2) | 94 (±6) | 95 (±5) | 92 (±9) | 81 (±5) |
| Methadone | 96 (±3) | 97 (±9) | 97 (±3) | 87 (±3) | 78 (±2) |
| Malathion | 101 (±6) | 98 (±8) | 89 (±4) | 81 (±1) | 80 (±5) |
| Diazepam | 98 (±7) | 96 (±7) | 83 (±4) | 80 (±7) | 78 (±5) |
| Cocaine | 100 (±7) | 101 (±1) | 91 (±5) | 92 (±7) | 87 (±5) |
| Myclobutanil | 95 (±5) | 97 (±5) | 87 (±5) | 84 (±39) | 80 (±5) |

In the preceding description, any discussion of a range of values should be understood to disclose all possible values within the range and all possible ranges falling with the range. For example, a discussion of "from about 1 to about 100" should be understood to be a disclosure of every value from about 1 to about 100 (for example 2, 10.7, 50, 80.5, and 92) and every range that falls between about 1 and about 100 (for example 10-20, 5-95, 75-80.5, and 24.3-47.5).

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A solid-phase micro-extraction (SPME) sample instrument comprising:
    a support; and
    an extraction coating covering at least a portion of the support, wherein the extraction coating comprises a sorptive particulate material immobilized in a fluorocarbon polymer that is a copolymer of tetrafluoroethylene and 2,2-bistrifluoromethyl-4,5-difluoro-1,3-dioxole, and
    wherein the sorptive particulate material comprises hydrophilic-lipophilic-balance particles which comprise the copolymerization polymer product of N-vinylpyrrolidinone and divinylbenzene.

2. The SPME sample instrument according to claim 1, wherein the support is a metal support, a metal alloy support, a fused silica support, a plastic support, a fluoro-plastic support, or a carbon material support.

3. A method of solid-phase micro-extraction (SPME) comprising:
    extracting at least one analyte from a sample matrix by exposing the extraction coating of the SPME sample instrument according to claim 1 to the sample matrix that comprises the at least one analyte; and
    desorbing the extracted analyte from the extraction coating.

4. The method according to claim 3, wherein the desorbing comprises exposing the extraction coating to: (i) a thermal-assisted desorption temperature, such as a temperature up to 300° C., and the method optionally further comprises gas chromatography or direct coupling to a spectroscopic technique suitable for detection of a thermally stable analyte, such as mass spectrometry; (ii) a solvent-assisted desorption solvent, and the method optionally further comprises liquid chromatography, gas chromatograph, capillary electrophoresis, or any spectroscopic technique suitable for determination of a solvent stable analyte; or (iii) electrothermal vaporization, arc and spark ablation, laser ablation, glow discharge, matrix-assisted laser desorption/ionization (MALDI), or desorption electrospray ionization (DESI), and the method optionally further comprises a spectroscopic technique, such as gas chromatography or direct coupling to mass spectrometry, suitable for detection of the analyte.

5. The SPME sample instrument according to claim 1, wherein the tetrafluoroethylene and the 2,2-bistrifluoromethyl-4,5-difluoro-1,3-dioxole are in a ratio of 13:87 or a ratio of 35:65.

6. The SPME sample instrument according to claim 1, wherein the sorptive material is a porous material having meso-, macro-, or micro-pores.

7. The SPME sample instrument according to claim 1, wherein the sorptive material has a surface area of about 10 m$^2$/g to about 3000 m$^2$/g.

8. The SPME sample instrument according to claim 7, wherein the sorptive material has a surface area of about 200 m$^2$/g to about 800 m$^2$/g.

9. The SPME sample instrument according to claim 5, wherein: the fluorocarbon polymer is a copolymer of tetrafluoroethylene and 2,2-bistrifluoromethyl-4,5-difluoro-1,3-dioxole in the ratio of 13:87.

\* \* \* \* \*